(12) United States Patent
Hermosillo Valadez et al.

(10) Patent No.: US 12,008,759 B2
(45) Date of Patent: Jun. 11, 2024

(54) METHOD AND SYSTEM FOR IDENTIFYING PATHOLOGICAL CHANGES IN FOLLOW-UP MEDICAL IMAGES

(71) Applicant: Siemens Healthcare GmbH, Erlangen (DE)

(72) Inventors: Gerardo Hermosillo Valadez, West Chester, PA (US); Sven Kohle, Erlangen (DE); Christian Tietjen, Fuerth (DE); Matthias Wolf, Coatesville, PA (US)

(73) Assignee: Siemens Healthineers AG, Forchheim (DE)

( * ) Notice: Subject to any disclaimer, the term of this patent is extended or adjusted under 35 U.S.C. 154(b) by 486 days.

(21) Appl. No.: 17/101,069

(22) Filed: Nov. 23, 2020

(65) Prior Publication Data

US 2021/0166391 A1 Jun. 3, 2021

(30) Foreign Application Priority Data

Nov. 29, 2019 (EP) ..................................... 19212525

(51) Int. Cl.
*G06T 7/00* (2017.01)
*G06N 3/08* (2023.01)
(Continued)

(52) U.S. Cl.
CPC ............. *G06T 7/0016* (2013.01); *G06N 3/08* (2013.01); *G06T 7/38* (2017.01); *G16H 30/20* (2018.01);
(Continued)

(58) Field of Classification Search
CPC ..... G06T 7/0012; G06T 7/0014; G06T 7/337; G06T 2207/30016; G06T 7/90;
(Continued)

(56) References Cited

U.S. PATENT DOCUMENTS

2007/0003117 A1* 1/2007 Wheeler ............... G06T 7/0012
382/128
2011/0081066 A1 4/2011 Jolly et al.
(Continued)

FOREIGN PATENT DOCUMENTS

| CN | 109003267 A | 12/2018 |
| CN | 110234394 A | 9/2019 |
| EP | 3554631 A2 | 10/2019 |

OTHER PUBLICATIONS

Havaei Mohammad et al: "Deep Learning Trends for Focal Brain Pathology Segmentation in MRI"; Dec. 10, 2016 (Dec. 10, 2016), International Conference on Simulation, Modeling, and Programming for Autonomous Robots, SIMPAR 2010; [Lecture Notes in Computer Science; Lect.Notes Computer], Springer, Berlin, Heidelberg; pp. 125-148, XP047365040; ISBN: 978-3-642-17318-9; 2016.
(Continued)

*Primary Examiner* — Ajibola A Akinyemi
(74) *Attorney, Agent, or Firm* — Harness, Dickey & Pierce, P.L.C.

(57) ABSTRACT

A computer-implemented method for identifying pathological changes in follow-up medical images is provided. In an embodiment, the method includes: providing reference image data showing a body part of a patient at a first time; providing follow-up image data showing a body part of a patient at a subsequent second time; generating one or more deformation fields for the reference image data and the follow-up image data describing anatomical deformations in the body part between the reference image data and the follow-up image data using at least one image registration; aligning the reference image data and the follow up image data using the one or more deformation fields to generate co-aligned image data; analyzing the co-aligned image data to identify pathological changes in the body part from the reference image data to the follow image data using a
(Continued)

machine learned network trained to recognize pathological relevant changes in co-aligned image data.

21 Claims, 5 Drawing Sheets

(51) Int. Cl.
  *G06T 7/38* (2017.01)
  *G16H 30/20* (2018.01)
(52) U.S. Cl.
  CPC .............. *G06T 2207/10088* (2013.01); *G06T 2207/20081* (2013.01); *G06T 2207/20084* (2013.01); *G06T 2207/20224* (2013.01)
(58) Field of Classification Search
  CPC . G06T 2207/10088; G06T 2207/30004; G06T 2207/10024; G06T 2207/10081; G06T 2207/20128; G06T 2207/30008; G06T 7/33; G06T 7/60; G06T 7/11; G06T 7/70; G06T 7/74; G06T 11/001; G06T 2207/10028; G06T 2207/20036; G06T 2207/20081
  USPC ......................................................... 382/131
  See application file for complete search history.

(56) References Cited

U.S. PATENT DOCUMENTS

| | | |
|---|---|---|
| 2012/0235679 A1 | 9/2012 | Xue et al. |
| 2016/0300120 A1* | 10/2016 | Haas ........................ G06T 7/149 |
| 2017/0217102 A1 | 8/2017 | Mansi et al. |
| 2018/0160933 A1 | 6/2018 | Bomzon |
| 2020/0268339 A1* | 8/2020 | Hao ........................ G06T 7/0014 |
| 2021/0158525 A1* | 5/2021 | Iwase ................... A61B 3/0025 |

OTHER PUBLICATIONS

Extended European Search Report dated May 28, 2020.

* cited by examiner

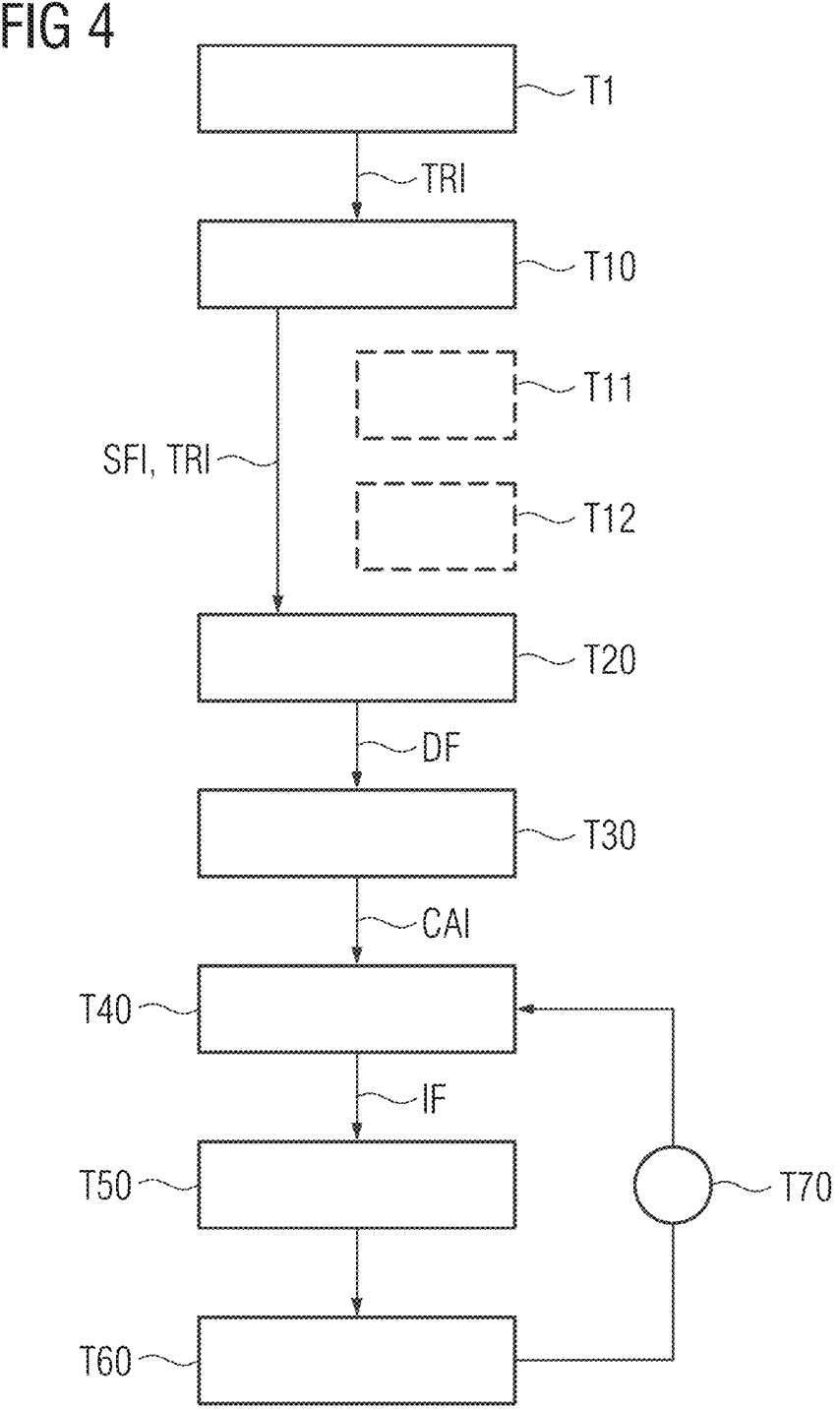

METHOD AND SYSTEM FOR IDENTIFYING PATHOLOGICAL CHANGES IN FOLLOW-UP MEDICAL IMAGES

PRIORITY STATEMENT

The present application hereby claims priority under 35 U.S.C. § 119 to European patent application number EP19212525.0 filed Nov. 29, 2019, the entire contents of which are hereby incorporated herein by reference.

FIELD

Embodiments of the invention generally relate to medical image processing, such as image processing for computed tomography images or magnetic resonance images.

BACKGROUND

Automated image processing for follow up reading and longitudinal change assessment is an important task in medical imaging techniques such as computed tomography (CT) or magnetic resonance imaging (MRI). The task of recognizing changes in medical images is a technical problem due to the challenge of distinguishing pathological from normal changes in the medical images. For example, for a follow up scan of a lung or other organ of a patient, normal anatomic changes such as respiration or other anatomical differences may mask pathological changes such as cancerous nodule growth or shrinkage.

Detecting pathological changes in CT images or MRI images acquired at two or more time points is difficult due to the large amount of normal changes that may occur. Manual detection of normal against pathological changes may be difficult or error prone. Computer-assisted image registration may be used to provide an improvement and increase in objectivity of the results. Image registration may be categorized into two groups: rigid and non-rigid. Non-rigid image registration is also known as deformable image registration. In rigid image registration, all pixels move and/or rotate uniformly so that every pixel-to-pixel relationship remains the same before and after transformation. In non-rigid image registration, however, the pixel-to-pixel relationships change to model a non-linear deformation.

Rigid image registration is very effective in cases when no anatomic change or deformations are expected. However, some patients may experience anatomical structure changes due to weight loss, tumor shrinkage, and/or physiological organ shape variation. These changes are usually not handled well by rigid image registration. In comparison to rigid image registration, non-rigid image registration has a significantly greater flexibility as non-rigid image registration can manage local distortion between two image sets (e.g. anatomical structure changes).

The methods, however, do not distinguish between normal anatomical changes and pathological changes. In an example, the recognition of a growing tumor may be suppressed in a follow up image if the degree of smoothing inevitably comprised in non-rigid image registration is too strong. Another issue associated with computer-implemented image registrations is that not all anatomies or organs can be equally well captured. While there exists a number of image registration models optimized for certain major anatomies or organs, such as lung, heart, liver, kidneys, spleen, or brain, other structures such as lymph nodes, main vessels, large and small intestine or pancreas are lacking dedicated registrations. This may be due to the fact that these structures are smaller, inherently more dynamic or more distributed. What is more, boundaries to other organs are usually not handled well by computer assisted image registration techniques.

SUMMARY

As soon as more than one single dedicated organ shall be analyzed in a so-called "whole body(-part) change visualization image", the inventors have discovered that all this brings about the problem that not only the desired pathological changes are highlighted after image post-processing, but also many visual artifacts. These artifacts may be introduced due to motion (e.g., heartbeat, breathing and flatulence), metal artifacts and/or weight loss. Further artifacts stem from organ boundaries physically moving along each other, e.g., lung pleura against rib cage. Especially when it comes to analyzing more than just the changes in one single organ, many of the current computer assisted methods are inaccurate and fail to distinguish abnormal changes from normal changes. As such, they provide inconsistent and confusing image registration.

Embodiments of the present invention are directed to a computer-aided diagnosis tool which supports a user/physician/radiologist/pathologist in deriving a medical diagnosis from a medical image volume, in particular, by appropriately highlighting pathological changes between follow up medical image scans. In particular, at least one embodiment of the present invention provides an improved computer-implemented method of distinguishing pathological changes from anatomical (i.e., normal, healthy) deformations in follow-up medical images. In this regard, it is furthermore desired in at least one embodiment to provide methods (and associated systems) which can deliver a comprehensive picture of pathological changes in medical images depicting a plurality of organs and anatomies within a body part of a patient and thereby assist physicians in medical diagnosis.

Embodiments are directed to a method for identifying pathological changes in follow-up medical images, a corresponding system, a corresponding method for training a machine learned network, a corresponding computer-program product and a computer-readable storage medium according to the independent claims. Alternative and/or preferred embodiments are object of the claims.

In the following, technical solutions according to embodiments of the present invention are described with respect to the apparatus embodiments as well as with respect to the method embodiments. Features, advantages or alternative embodiments described herein can likewise be assigned to other claimed objects and vice versa. In other words, claims and embodiments addressing the inventive method can be improved by features described in embodiments or claimed with respect to the apparatuses. In this case, e.g., functional features of the method are embodied by objective units or elements of the apparatus.

According to an embodiment, a computer-implemented method for identifying pathological changes in follow-up medical images is provided. The method comprises several steps. A first step is directed to providing (or receiving) reference image data showing a body part of a patient at a first time. A further step is directed to providing (or receiving) follow-up image data showing a body part (or the body part) of a patient (or the patient) at a subsequent second time. Further, the method comprises the step of generating one or more deformation fields for the reference image data and the follow-up image data describing anatomical deformations in the body part between the reference image data and the follow-up image data using at least one image registration. In a further step, the reference image data and the follow up image data are aligned using the one or more deformation fields to generate co-aligned image data. Yet a further step is directed to analyzing the co-aligned image data to identify pathological changes in the body part from the reference image data to the follow image data using a machine learned network trained to identify pathological relevant changes (i.e., pathological changes) in co-aligned image data.

That being said, according to a further embodiment, a method for training a machine learned network to recognize pathological relevant changes in co-aligned image data is provided comprising a plurality of steps. A first step is directed to provide training reference image data showing a body part of a patient. A second step is directed to generate simulated follow-up image data by deforming the training reference image data using one or more models for biomechanical soft tissue deformation and, optionally, including one or more simulated pathological changes (and, further optionally, simulated artifacts in the deformation). That followed, one or more deformation fields for the training reference image data and the simulated follow-up image data describing anatomical deformations in the body part between the training reference image data and the simulated follow-up image data are calculated using one or more image registrations. A further step is directed to aligning the training reference image data and the simulated follow-up image data using the one or more deformation fields to generate co-aligned image data, followed by analyzing the co-aligned image data to identify pathological changes in the body part from the training reference image data to the simulated follow-up image data using a machine learned network. A further step is directed to compare the result with the known input generated by the one or more models for biomechanical soft tissue deformation and adjusting weights in the neural network as a function of the comparison.

According to an embodiment, a system for identifying pathological changes in follow-up medical images is provided. The system comprises an interface unit for receiving reference image data showing a body part of a patient at a first time and follow-up image data showing a body part of a patient at a subsequent second time. Further the system comprises a computing unit configured to: receive reference image data and follow-up image data, generate one or more deformation fields for the reference image data and the follow-up image data describing anatomical deformations in the body part between the reference image data and the follow-up image data using at least one image registration, align the reference image data and the follow up image data using the one or more deformation fields to generate co-aligned image data, and analyze the co-aligned image data to identify pathological changes in the body part from the reference image data to the follow image data using a machine learned network trained to recognize pathological relevant changes in co-aligned image data.

According to an embodiment, the system is adapted to implement an embodiment of the inventive method for identifying pathological changes in follow-up medical images. The computing unit may comprise an image registration unit configured to generate the one or more deformation fields using at least one image registration. Optionally, the registration unit may further be configured to generate the one or more deformation fields additionally based on one or more biomechanical models of soft tissue deformation. The computing unit may further comprise an aligning unit configured to generate the co-aligned image data. The computing unit is further configured to run a machined learned network for analyzing the co-aligned image data for distinguishing pathological relevant changes from anatomical deformations and artifacts stemming from the generation of the one or more deformation fields. The computing unit may further comprise a visualization unit configured to generate a visualization (for a user) highlighting the identified pathological changes against anatomical deformations and any artifacts included in the co-aligned image data, e.g., in the form of the aforementioned change visualization image data.

According to another embodiment, the invention further relates to a training system for training a machine learned network, comprising an interface, embodied for receiving the machine learned network, and further embodied for receiving training reference image data showing a body part of a patient. The training system further comprises a processor configured to generate simulated follow-up image data by deforming the training reference image data using one or more models for biomechanical soft tissue deformation and, optionally, including one or more simulated pathological changes (and, further optionally, artifacts in the deformation). The processor is further configured to calculate one or more deformation fields for the training reference image data and the simulated follow-up image data describing anatomical deformations in the body part between the training reference image data and the simulated follow-up image data. The processor is further configured to align the training reference image data and the simulated follow-up image data using the one or more deformation fields to generate co-aligned image data, and to analyze the co-aligned image data to identify pathological changes in the body part from the training reference image data to the simulated follow-up image data using a machine learned network. The processor is further configured to compare the result with the known input generated by the one or more models for biomechanical soft tissue deformation and adjusting the weights in the neural network as a function of the comparison.

According to another embodiment, the invention further relates to an image analysis system comprising the system for identifying pathological changes in follow-up medical images and a medical image system configured to acquire, store and/or forward follow-up medical images (comprising the reference image data and the follow-up image data). Thereby, the interface unit is configured to receive the reference image data and follow-up image data from the medical image system.

According to an embodiment, the medical image system comprises one or more archive stations for storing reference image data RI and/or follow-up image data FI, which may be realized as a cloud storage or as a local or spread storage, e.g., as a PACS (Picture Archiving and Communication System). Further, the medical image system may comprise one or more medical imaging modalities, such as a computed tomography system, a magnetic resonance system, an angiography (or C-arm X-ray) system, a positron-emission tomography system, a mammography system, system for acquiring digital pathology images or the like.

According to another embodiment, the present invention is directed to a computer program product comprising program elements which induce a computing unit of a system for quantifying a medical image volume to perform the steps according to an embodiment of the method, when the program elements are loaded into a memory of the computing unit.

According to another embodiment, the present invention is directed to a computer-readable medium on which program elements are stored that are readable and executable by a computing unit of a system for quantifying a medical image volume, in order to perform steps of an embodiment of the inventive method, when the program elements are executed by the computing unit.

According to another embodiment, the present invention is directed to a computer-implemented method for identifying pathological changes in follow-up medical images, the method comprising:

providing reference image data showing a body part of a patient at a first time;

providing follow-up image data showing the body part of the patient at a subsequent second time;

generating one or more deformation fields for the reference image data and the follow-up image data describing anatomical deformations in the body part between the reference image data and the follow-up image data, using at least one image registration;

aligning the reference image data and the follow up image data using the one or more deformation fields generated, to generate co-aligned image data; and analyzing the co-aligned image data to identify pathological changes in the body part from the reference image data to the follow image data using a machine learned network trained to identify pathological relevant changes in co-aligned image data.

According to another embodiment, the present invention is directed to a method for training a machine learned network to identify pathological relevant changes in follow-up medical images, the method comprising:

providing training reference image data showing a body part of a patient;

generating simulated follow-up image data by deforming the training reference image data using one or more models for biomechanical soft tissue deformation;

calculating one or more deformation fields for the training reference image data and the simulated follow-up image data describing anatomical deformations in the body part between the training reference image data and the simulated follow-up image data using at least one image registration;

aligning the training reference image data and the simulated follow-up image data using the one or more deformation fields to generate co-aligned image data;

analyzing the co-aligned image data to identify any pathological changes in the body part from the training reference image data to the simulated follow-up image data using the machine learned network;

comparing a result of the analyzing with a known input based on the one or more models; and adjusting weights in the neural network as a function of the comparing.

According to another embodiment, the present invention is directed to a system for identifying pathological changes in follow-up medical images, comprising:

an interface unit to receive reference image data showing a body part of a patient at a first time and follow-up image data showing the body part of the patient at a subsequent second time;

a computing unit configured to:
receive reference image data and follow-up image data;
generate one or more deformation fields for the reference image data and the follow-up image data describing anatomical deformations in the body part between the reference image data and the follow-up image data using at least one image registration;
align the reference image data and the follow up image data using the one or more deformation fields to generate co-aligned image data; and
analyze the co-aligned image data to identify pathological changes in the body part from the reference image data to the follow image data using a machine learned network trained to recognize pathological relevant changes in co-aligned image data.

According to another embodiment, the present invention is directed to a non-transitory computer program product storing program elements which induce a computing unit of a system for identifying pathological changes in follow-up medical images, to perform the method of an embodiment, when the program elements are loaded into a memory of the computing unit and executed.

According to another embodiment, the present invention is directed to a non-transitory computer-readable medium storing program elements, readable and executable by a computing unit of a system for identifying pathological changes in follow-up medical images, to perform the method of an embodiment, when the program elements are executed by the computing unit.

BRIEF DESCRIPTION OF THE DRAWINGS

Characteristics, features and advantages of the above de-scribed invention, as well as the manner they are achieved, become clearer and more understandable in the light of the following description and embodiments, which will be described in detail with respect to the figures. This following description does not limit the invention on the contained embodiments. Same components or parts can be labeled with the same reference signs in different figures. In general, the figures are not drawn to scale. In the following:

FIG. 4 depicts a flowchart illustrating a method for training a machine learned network according to an embodiment.

DETAILED DESCRIPTION OF THE EXAMPLE EMBODIMENTS

Figure 1:
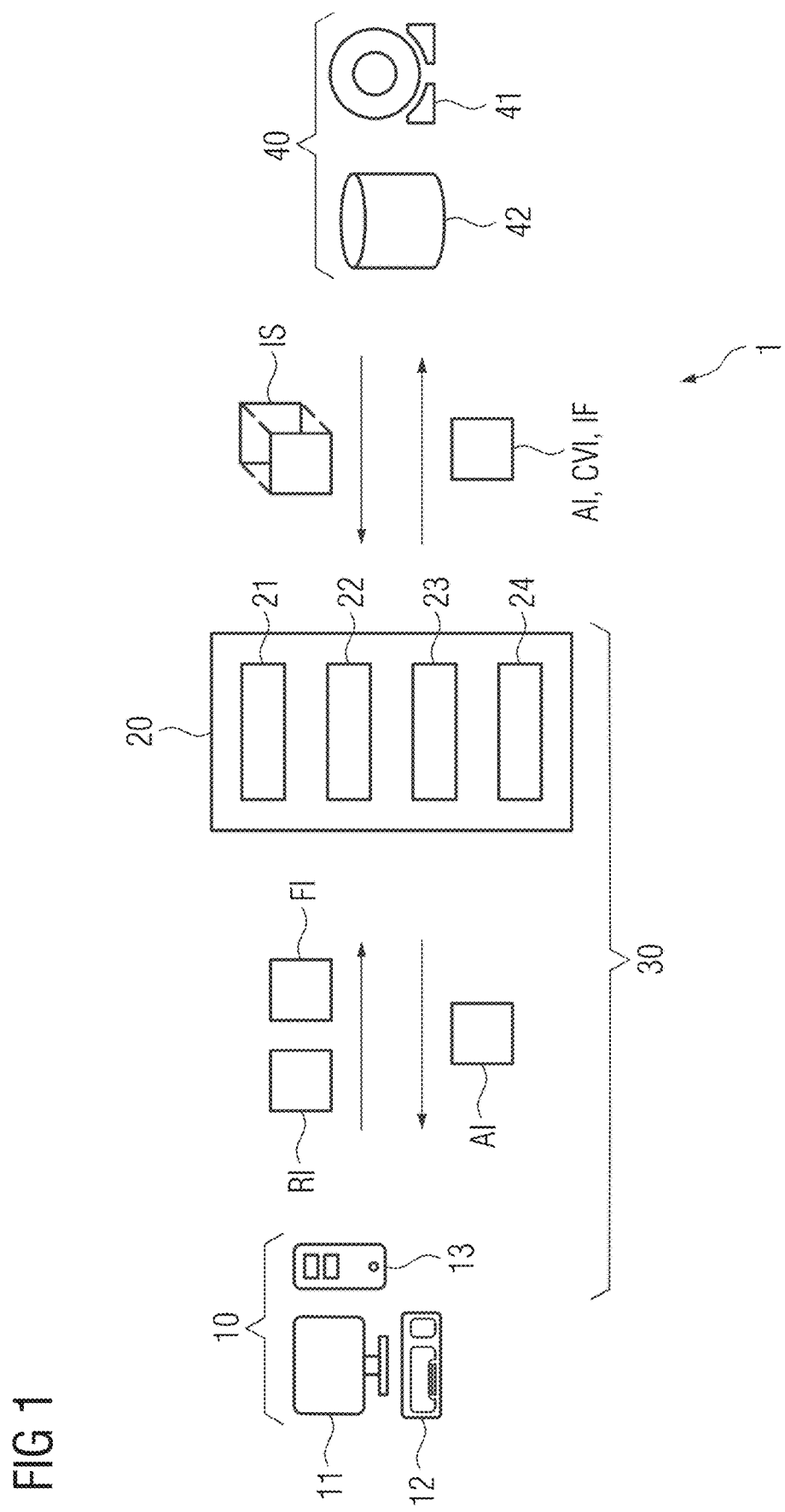
FIG. 1 depicts a system for identifying pathological changes in follow up medical image data according to an embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to an embodiment, a computer-implemented method for identifying pathological changes in follow-up medical images is provided. The method comprises several steps. A first step is directed to providing (or receiving) reference image data showing a body part of a patient at a first time. A further step is directed to providing (or receiving) follow-up image data showing a body part (or the body part) of a patient (or the patient) at a subsequent second time. Further, the method comprises the step of generating one or more deformation fields for the reference image data and the follow-up image data describing anatomical deformations in the body part between the reference image data and the follow-up image data using at least one image registration. In a further step, the reference image data and the follow up image data are aligned using the one or more deformation fields to generate co-aligned image data. Yet a further step is directed to analyzing the co-aligned image data to identify pathological changes in the body part from the reference image data to the follow image data using a machine learned network trained to identify pathological relevant changes (i.e., pathological changes) in co-aligned image data.

Reference and follow-up medical images may relate to two-dimensional data sets providing two dimensions in space. Further, reference and follow-up medical images may relate to three-dimensional data sets providing three dimensions in space. The reference and follow-up medical image data depict a body part of a patient in the sense that they contain a two- or three-dimensional image data of the patient's body part (i.e., follow-up and reference image generally show the same body part of the same patient). Reference and follow-up medical image data may, for example, be in the form of an array of pixels or voxels. Such arrays of pixels or voxels may be representative of intensity, absorption or other parameter as a function of three-dimensional position, and may, for example, be obtained by suitable processing of measurement signals obtained by a medical imaging modality. A medical imaging modality corresponds to a system used to generate or produce medical images. For example, a medical imaging modality may be a computed tomography system (CT system), a magnetic resonance system (MR system), an angiography (or C-arm X-ray) system, a positron-emission tomography system (PET system) or the like.

Specifically, computed tomography is a widely used imaging method and makes use of "hard" X-rays produced and detected by a specially rotating instrument. The resulting attenuation data (also referred to as raw data) is presented by a computed analytic software producing detailed images of the internal structure of the patient's body parts. The produced sets of images are called CT-scans which may constitute multiple series of sequential images to present the internal anatomical structures in cross sections perpendicular to the axis of the human body.

Magnetic Resonance Imaging (MRI), to provide another example, is an advanced medical imaging technique which makes use of the effect magnetic field impacts on movements of protons. In MRI machines, the detectors are antennas and the signals are analyzed by a computer creating detailed images of the internal structures in any section of the human body. Accordingly, the depicted body part of the patient in general will comprise a plurality of anatomies and/or organs. Taking a chest image as an example, reference and follow-up image data may show lung tissue, the rib cage, lymph nodes and others. "Providing" in the framework of the application may mean that reference and follow-up image data are acquired from the medical imaging modalities. Further providing may mean that they are acquired from an appropriate memory such as an picture archiving and communication system (PACS) or any other suitable medical image storing facility. Further providing may mean that the reference and follow-up image data are merely received for further processing.

Since reference and follow-up image data relate to images acquired at different times, there will be changes visible from the reference image data to the follow-up image data. In principle, two types of changes can be defined. One type of changes are the anatomical changes or deformations. These changes relate to normal or "healthy" changes. One example for such anatomical deformations relates to the breathing motion of lung tissue. As a patient inhales or exhales, the shape of the lung changes. Thereby, the lower portions of the lungs may exhibit larger deformations than, for example, the center of the lung. As the lung deforms, neighboring tissue will likewise undergo anatomical deformations.

Another example for anatomical deformations—albeit taking place at much longer time scales—would be (normal) weight loss or gain of a patient. The anatomical changes have to be contrasted with pathological deformations or changes that often relate to a disease state. Examples include the growth or shrinkage of nodules, the occurrence of new nodules and/or lesions and so forth. While pathological changes are highly relevant information for the physician when formulating a medical diagnosis, anatomical deformations are less relevant or even irrelevant as they relate to "healthy" deformations of less or little pathological relevance. To appropriately assist the physician (or radiologist or any other user for that matter) in coming up with a medical diagnosis, the anatomical deformations have to be delineated from the pathological deformations, or, in other words, the anatomical deformations have to be filtered out. This requires the method to identify the difference between anatomical and pathological changes.

To this end, the method of at least one embodiment essentially foresees to a apply a two-steps approach. In a first step, deformation fields indicative of the anatomical deformations are calculated using one or more image registrations. As explained before, these deformation fields will in most cases contain artifacts mainly stemming from inaccurate image registrations and boundary effects. In a second step, the outcome of the image registration (i.e., all deformation fields and motion models used during image registration and so forth) together with the underlying image data (i.e., follow-up image data and/or reference image data) will be provided to a trained function in the form of a machine learned network. The machine learned network is trained to recognize artifacts created in the image registration step (e.g., erroneous or unphysical deformations in the calculated deformation fields and/or mismatches in fitting the motion models, etc.) and/or to recognize the pathological relevance of the remaining changes, or, in other words, to recognize pathological changes on the basis of the input information.

The step of generating (or, in other words calculating) a deformation field by using one or more image registrations may thus be seen as a first estimate about the anatomical changes. In particular, this may include applying a plurality of image registrations, e.g., a designated image registration for each anatomy identified in the depicted patient's body part. Image registration as such is a well-known method in the art. Essentially, this includes registering an image with a corresponding image of a time series and finding a deformation field between the two images that determines a relationship between the coordinate systems of the reference image data and the follow-up image data such that each anatomical location in the reference image data is mapped to the same anatomical location in the follow-up image data. Thus, the deformation field may comprise a plurality of individual displacement vectors respectively associated with the voxels of reference image data and follow-up image data.

A rigid registration in this context may comprise a registration in which the coordinates of data points in one data set are subject to rotation and translation in order to register the data set to another data set. An affine registration in this context may comprise a registration in which the coordinates of data points in one dataset are subject to rotation, translation, scaling and/or shearing in order to register the dataset to another dataset. Thus, a rigid registration may be considered to be a particular type of affine registration.

Non-rigid registrations, by contrast, can provide different displacements for each voxel of the data set to be registered and can, for example, use non-linear transformations, in which the coordinates of data points in one dataset are subject to flexible deformations in order to register the data set to another data set. Non-linear transformations may in some cases be defined using vector fields such as warp fields, or other fields or functions, defining an individual displacement for each voxel in a three-dimensional data set. For more detailed information about image registration, reference is made to US 2011/0 081 066 and US 2012/0 235 679, the entire contents of each of which are hereby incorporated herein by reference. The one or more image registrations used according to the first embodiment may be rigid image registrations, non-rigid image registrations and combinations thereof.

Once a first estimate of the anatomical deformations has been acquired in terms of the deformation fields, the deformation fields are used to align the reference image data with the follow-up image data. The alignment is used to identify pathological differences between the two data sets. The aligning may include applying the deformation fields to the reference image data to generate a deformed prior image or deformed reference image data as the co-aligned image data.

Further, the step of aligning may include applying the deformation field (as inverse deformation field) to the follow-up image data to generate deformed follow-up image data. Moreover, the co-aligned image data may also relate to data where the follow-up image data and/or reference image data are registered with the deformation field, e.g., so that a displacement is assigned to each pixel or voxel of follow-up image data and/or reference image data.

In general, the co-aligned image data thus relates the calculated deformation field(s) to the visual information contained in the follow-up image data and/or reference image data. As such, the co-aligned reference image may be conceived as constituting filtered image data in which the anatomical deformations have been filtered out. As the deformation field obtained by the one or more image registrations is prone to still contain artifacts, also the estimate of the anatomical changes will comprise artifacts in the form of faults, unphysical distortions and inaccuracies, however.

In a next step, the co-aligned image data is provided to the machine learned network. As explained, the co-aligned image data comprises information about the deformation field and part or all of the image content information that was used to generate the deformation field in the first place. The machine learned network is trained to use this information and identify pathological changes between the follow-up image data and the reference image data. To do so, it may be trained to recognize artifacts in the deformation fields (i.e., artifacts stemming from the step of generating) by comparing it to the underlying image data.

The training of the neural network may make use of the fact that artifacts in the deformation field are still present after the images have been aligned and that these can be readily related to the underlying image data. Hence, artifacts in the deformation field may readily be recognized as such when compared to the underlying image data. For instance, the machine learned network may check if distortions or singularities in the deformation field(s) fall onto boundaries visible between organs or anatomies as this might indicate that irregularities in the deformation stem from artifacts in the image registration. Besides, the machine learned network may be trained to recognize pathological changes (or, in other words, disease patterns) characterized by visual image features. In this regard, the machine learned network may flag deformations as relating to pathological changes when they occur within an otherwise homogenous image segment, for instance.

Preferably, the machine learned network is a machine learned (artificial) neural network, most preferably a convolutional neural network. A neural network is basically built up like a biological neural net, e.g., a human brain. In particular, an artificial neural network comprises an input layer and an output layer. It may further comprise a plurality of layers between input and output layer. Each layer comprises at least one, preferably a plurality of nodes. Each node may be understood as a biological processing unit, e.g., a neuron. In other words, each neuron corresponds to an operation applied to input data. Nodes of one layer may be interconnected by edges or connections to nodes of other layers, in particular, by directed edges or connections. These edges or connections define the data flow between the nodes of the network.

In particular, the edges or connections are equipped with a parameter, wherein the parameter is often denoted as "weight". This parameter can regulate the importance of the output of a first node to the input of a second node, wherein the first node and the second node are connected by an edge. In particular, a neural network can be trained. In particular, training of a neural network is performed based on known pairs of input and output values according to a 'supervised learning' technique, wherein the known input values are used as inputs of the neural network, and wherein the corresponding output value of the neural network is compared to the corresponding known output value. The artificial neural network independently learns and adapts the weights for the individual nodes as long as the output values of the last network layer sufficiently correspond to the known output values according to the trainings data. For convolutional neural networks, this technique is also called 'deep learning'. The terms 'neural network' and 'artificial neural network' can be used as synonyms.

A first group of neural network layers may be applied to extract features from images. In this case, image data such as the deformed reference image data or deformed follow-up image data, i.e., the gray scale and/or color values for each individual image element of the image, and/or serve as input values for the neural network. In addition, corresponding features may be extracted from the deformation field. The thus extracted features like, contrast, gradients, texture, density, distortion, singularities, gradients, or the like may be fed as input values to a second group of network layers also known as classifiers which serve to further assign objects and/or characteristics to at least one of the extracted features present in the image. However, both functions of the described neural network may likewise be carried out by separated, individual neural networks. In other words, image analysis for feature extraction can be carried out by a first neural network, and classification, i.e., object and/or characteristic assignment can be carried out by a second neural network.

In particular, the machine learned neural network may be a convolutional neural network. In particular, the machine learned neural network may be a deep convolutional neural network. In one example, a fully convolutional, image-to-image neural network may be used in which the co-aligned image data is input into the network, and the output is a filter image or a likelihood map of pathological changes. Any type of image-to-image neural network may be used. Alternative machine-learned networks may be used that are configured or trained to identify pathological changes if provided with deformation fields and corresponding medical image data.

According to an implementation, the machine learned neural network comprises one or more convolutional layers and/or one or more deconvolutional layers. Further, the machine learned neural network may comprise one or more pooling layers and/or one or more up-sampling layers. Further, the machine learned neural network may comprise one or more fully connected layers.

The inventors have recognized that, through the use of convolutional layers and/or deconvolutional layers, a neural network can be employed especially efficiently for image processing, since despite many connections between node layers, only a few edge weights (namely the edge weights corresponding to the values of the convolutional kernel) have to be determined by training. With a same number of training data, the accuracy of the neural network can thus also be improved.

The network may be trained using ground truth data comprising reference image data and follow-up image data in which pathological changes have been manually annotated. This ground truth data may then be processed in the same way as explained in connection with the above method, i.e., by generating the deformation fields and the co-aligned image data, and by inputting the co-aligned image data to the machine learned model. The indications of pathological changes as provided by the machine learned network on that basis may then be compared to the manually annotated changes. The comparison (e.g., difference), namely the loss function, is used to provide feedback to the network so that weights of the network may be adjusted to generate a better indication of the pathologically relevant changes. Further, as will be further detailed below, the network may be trained using artificially generated follow-up image data (or reference image data) from existing reference image data (or follow-up image data) using a motion model for simulating anatomic deformations.

Being trained to recognize pathological changes and/or artifacts stemming from the step of generating the displacement fields in other words means that the machine learned network is trained to distinguish pathological changes from anatomical changes and artifacts, e.g., arising from the image registration. As such, the machine learned network can further be seen as being trained to recognize artifacts and/or anatomical changes/deformations. The network's ability to identify pathological changes may mean that it is trained to (merely) recognize artifacts and/or anatomic deformations in the co-aligned image data. The identification of the pathological relevant changes may then be conceived as an implicit "by-product" of the artifact recognition as all residual changes will automatically relate to pathological changes.

Moreover, the machine learned network may be trained to positively recognize pathological changes (which would go beyond merely recognizing artifacts). With that, it would become more readily possible to actively flag out pathological changes to the user (which might be barely visible otherwise). "Recognizing" in this context may mean that the machine learned network provides information about the position and involved voxels of the pathological changes in the reference image data and/or follow-up image data, the amount of change, and so forth.

In summary, in at least one embodiment, the method steps as introduced above synergistically contribute to a method that allows for a reliable identification of pathological changes in follow-up medical images. Accordingly, a method is provided that assists the user in providing a medical diagnosis by processing physiological measurements. Thereby, the processing is essentially divided into two interlinked steps: the computation of one or more deformation fields with the help of appropriate image registrations and the subsequent analysis of the results using artificial intelligence.

Basing the method on image registrations means that schemes and algorithms may be deployed which over the years have been thoroughly optimized for specific organs and anatomies and which have proven extremely powerful for specific tasks. Using image registrations has the further advantage that the starting point for the machine learned network is considerably improved which alleviates the training phase and improves the overall accuracy of the method. In turn, the implementation of a machine learned network makes it possible to readily verify and highlight the outcome of the method for the user.

What is more, the usage of the machine learned model is the precondition to readily use image registrations across different anatomies and/or to combine a plurality of image registrations. This is because the learned ability of distinguishing relevant from irrelevant changes inherently comprises an error correction for artifacts which are inevitable when image registrations are applied to whole body parts comprising a multitude of anatomies and structures. For the user, this is of considerable help since medical diagnoses are generally not exclusively focused on one organ only but require screening neighboring organs and tissue for cancerous ingrowths and metastases. By providing a comprehensive picture of the pathological changes in a body part, the method according to the first embodiment is able to optimally support the user in providing a medical diagnosis.

Of note, the method of at least one embodiment is not limited to compare precisely one reference image data set with one follow-up image data set. Rather, the steps may be applied repeatedly when comparing image data taken at more than two points in time, as may be the case when comparing follow-up image data at hand with two different reference image data sets.

According to an embodiment, the step of aligning comprises calculating deformed reference image data by applying the at least one deformation field to the reference image data.

By applying the deformation field to the reference image data, the reference image data is transformed into the "coordinate system" of the follow-up image data. In other words, the ensuing deformed reference image data is corrected for anatomic changes and deformations that happened in the period of time between acquisition of reference image data and follow-up image data. Not considering any artifacts in the deformation field, deformed reference image data and follow-up image data would in principle be already fit for a direct comparison to determine pathological changes between the two images. Such comparison might, for instance, comprise subtracting the deformed reference image data from the follow-up image data. As the deformed reference image data is still based on straight-forward image registration, which is prone to contain artifacts, however, any pathological changes comprised in the result would be barely discernible from the artifacts, in practice.

Still, the provision of the deformed reference image data constitutes an important intermediate result which has the twofold advantage that it can be readily processed by the machine learned network and provides a good basis for the ensuing presentation of the pathological changes to the user. Further, also in terms of training the machine learned model it constitutes a reasonable starting point, since deformed reference image data can be readily calculated for the available training data sets.

As an alternative, the step of aligning may likewise comprise calculating deformed follow-up image data by applying the at least one deformation field to the reference image data. Depending on the implementation of the image registration, this step might be supplemented by a step of inverting the deformation field.

According to an embodiment, the step of analyzing comprises generating an image filter corresponding to the co-aligned image data, the image filter being configured to highlight pathological changes based on the output of the machine learned network.

The image filter may be configured such that it constitutes image data compatible with reference image data and follow-up image data. In particular, the image filter may have the same or similar format and/or dimensions as the reference image data and/or the follow-up image data. The image filter may be configured such that when applied to reference image data and/or follow-up image data, the pathological changes are highlighted. For instance, the image filter may be configured such that it can be overlaid over reference image data and/or follow-up image data, or that it can be multiplied with reference image data and/or follow-up image data. The machine learned network might be configured as image-to-image network with the co-aligned image data as input and the image filter as output.

Highlighting pathological changes may mean that irrelevant changes such as residual artifacts stemming from the image registrations are filtered out (due to the machine learned network's ability to detect artifacts) and/or that relevant, i.e., pathological changes are highlighted (due to the machine learned network's ability to recognize pathological changes). Highlighting may mean that the pixels or voxels underlying a pathological change may be visually enhanced, e.g., in terms of color and/or brightness. Filtering out may mean that the pixels or voxels corresponding to artifacts are visually dimmed, e.g., by reducing their intensity or merging them with the background.

By generating an image filter for highlighting pathological changes, an output is provided which can be intuitively accessed by the user. It allows for a quick visual inspection of the pathological changes from one medical examination to the other.

According to an embodiment, the step of analyzing comprises subtracting the deformed reference image data from the follow-up image data and multiplying the result with the image filter.

The subtraction of the deformed reference image data from the follow-up image data generates image data which has been corrected for motions and deformations as identified by image registration. This image data is subsequently also denoted as subtraction image data. The subtraction image data retains the pathological changes. However, the deformed reference image data also contains artifacts stemming from erroneous image registration. Essentially, the subtraction image data is a two- or three-dimensional image in which pathological changes as well as artifacts may appear as non-zero entries (pixels or voxels).

To filter out artifacts, the subtraction image data is multiplied with the image filter. In turn, the image filter is configured so that it filters out artifacts in the subtraction image data. For instance, the image filter may contain zeros at places in the three-dimensional image data where artifacts have been identified. Moreover, the image filter may be configured to highlight pathological changes.

To this end, the image filter may contain enhancing factors at places in the two- or three-dimensional image data where pathological changes have been identified. Enhancing factors may be such that the intensity or brightness (e.g., in terms of the grey scale value) of the respective pixel or voxel is increased or that a color is changed or added to highlight the corresponding pixel or voxel against the background. The result of the above process (i.e., subtracting the deformed reference image from the follow-up image and multiplying the result with the image filter) may subsequently also denoted as "change visualization image data".

According to an embodiment, the step of generating further comprises segmenting the reference image data and follow-up image data to define a plurality of corresponding segment pairs within the reference image data and follow-up image data, each segment pair corresponding to a different anatomy of the patient's body part depicted in the reference image data and follow-up image data.

As mentioned, a body part of a patient usually comprises a plurality of anatomies and organs such as, taking a chest image as an example, lung lobes, rib structures, the spine, the heart and so forth. In many cases not all of these anatomies are relevant for a given diagnosis and, what is more, not all anatomies are handled equally well by available image processing algorithms. The segmentation in this context allows to identify anatomies and organs in the image data and delineate them against neighboring structures, background and unstructured tissue. This makes it possible to apply dedicated image analysis procedures that have been optimized for the specific organ.

Not only does this apply for the image registration (see below) but also for possible image pre-processing steps which happen upstream of the actual image registration. In addition, partitioning of reference image data and follow-up image data enables to interactively focus the analysis and the later display of information to the organs and anatomies of interest for the user, making the method more readily accessible to the user. For the image segmentation, in principle known methods can be used.

According to an embodiment, the step of generating comprises generating a plurality of deformation fields by separately applying image registrations to different segments (or pairs of segments) correspondingly defined in the reference image data and the follow-up image data.

In other words, different image registrations are used for different segments of the reference image data and follow-up image data. The usage of different image registrations on different segments enables to apply registrations specifically optimized for different anatomies such as lung, liver, kidneys, spleen, brain, bones, and many others. For segments for which no designated image registrations are available (e.g., lymph node, main vessels, large and small intestine, pancreas, etc.), general image registrations may be used. Likewise, general image registration techniques may be used for unstructured parts of the reference image data and follow-up image data, e.g., in order to cover the target anatomy plus its surroundings. Generally, each image registration will provide its own deformation field. All deformation fields together define the anatomical deformations from the reference image data to the follow-up image data as calculated by the image registrations. Of note, the segments may also overlap and so may the individual deformation fields. The machine learned network is trained to cope with such input.

The usage of different image registrations for different segments of reference image data and follow-up image data has the advantage that specialized routines may be deployed which usually perform better than more general models. Of note, the usage of a plurality of different image registrations is made possible by the subsequent implementation of the machine learned network for identifying the pathological artifacts in the first place. This is because the combination of different image registrations may lead to huge artifacts in the overall deformation field (in particular, at the boundaries of two anatomies where the individual deformation fields outputted by the individual image registrations have been pieced together). Without the ensuing filtering as effected by the machine learned network, a user would thus hardly be able to identify relevant pathological changes between reference image data and follow-up image data.

According to an embodiment, the method further comprises rendering an image of the follow up image data and displaying the image with the pathological changes highlighted.

By providing the user with a rendering of the follow up image data with the pathological changes highlighted, the user can immediately infer what changes happened and where these changes occurred. This helps guiding the image reading and therefore increases the usability of the method and provides an improved assistance to the user for deriving a medical diagnosis.

The two-dimensional rendering may, in general, rely on known rendering procedures, such as ray-casting, ray-tracing, texture-rendering or the like. The term "highlighted" in this context may mean that the pathological changes are visually enhanced in brightness, color, and/or intensity. In addition to that or as an alternative, the identified pathological changes may be highlighted using symbols. Further, the identified pathological changes may be highlighted using labels comprising semantic expressions. The highlighting or labeling may be carried out based on information from the machine learned network as to the identified pathological changes, such as position, volume and amount of change of the pathological changes. Displaying with the pathological changes highlighted may further mean that the rendered image of the follow up image data is displayed with the change visualization image data overlaid. Highlighting may furthermore mean using a heatmap wherein, e.g., the amount of change is color-coded. For instance, shrinking nodules may be assigned a different color than growing nodules. The heatmap may likewise be visualized as an overlay image on the follow up image data.

According to an embodiment, identifying pathological changes may comprise determining metadata associated to the pathological changes.

The metadata may be seen as auxiliary information providing additional insights as to the identified pathological changes. The metadata may relate to a type of change, such as indications of newly formed lesions or vanished lesions, to a pathology type, to a classification according to size and/or shape, to a classification according to malignant or benign, and/or to a classification according to behavior such growing or shrinking. The metadata may include semantic information describing the above parameters.

Further, the metadata may include numerical information such as the volume, cross-section, circumference, diameter, growth or shrinkage rates, values quantifying observables such as a state of the contour (e.g., either smooth or spiculated), a degree of calcification or fat deposition, or degree of solidity and the like of a underlying lesion, nodule, mass or other pathologically relevant feature. To retrieve the metadata upon identifying pathological changes, the machine learned network may be trained to determine (extract) the metadata from the co-aligned image data. In this regard, the training of the neural network may rely on expert-annotated data or on simulated pathological changes with known metadata.

According to an embodiment, the method further comprises labeling the pathological changes for a user on the basis of the metadata.

The labeling may be carried out in the above-mentioned rendering of the follow-up image data at positions of the identified pathological changes. As an alternative or in addition to that, the labeling may be carried out in the form of a list for a user, which lists the pathological changes in conjunction with the corresponding metadata. According to a further implementation, the pathological changes in the list may be ranked on the basis of the metadata. In doing so, the pathological changes may be prioritized. Specifically, the pathological changes may be ranked according to criteria such as the degree of malignancy or growth rate, thereby directing the attention of the user to the most relevant pathological changes. According to an implementation, the ranking criteria may be interactively set by the user.

According to an embodiment, also artifacts and/or anatomical changes may be identified to a user by appropriately labeling them.

According to an embodiment, the method further comprises determining an imaging window for reference and/or follow up image data, and rendering the follow-up image data on the basis of the determined imaging window (e.g., by rendering only those parts of the follow-up image data within the imaging window).

The imaging window may be determined by a user—or semi-automatically or automatically by the method for users who need more assistance. The term "imaging window" in general relates to the process of selecting only a part or parts of the follow-up image data and/or reference image data for display. This may include selecting only a part of the image segments (e.g., as determined in the aforementioned segmentation step) for display. It may further include defining an image intensity window and displaying only such intensities within the window. The latter example has considerable significance in CT imaging. Each voxel of CT image data usually has an intensity value (commonly measured in Hounsfield or HU units) that represents the attenuation of X-rays at the corresponding position in the volume as determined from the CT measurements. Due to this relation, a segmentation can be performed based solely on a thresholding of the voxel intensity values. For example, all voxels having intensity values in a particular range may be considered to represent bone. The corresponding range is called the "bone window". Other windows may relate to carve out soft tissue or lung parts. In the art, these windows are commonly referred to as HU-windows.

That being said, according to an embodiment, the reference image data and follow-up image data are computed tomography image data (i.e., have been acquired with a CT-system), and the method comprises determining a current HU window and rendering only those parts of the follow-up image data (and/or reference image date and/or change visualization data) laying within the current HU window.

In any case, constricting the displayed information to only those parts of the imaging volume which are currently under consideration, i.e., which lay within the imaging window, provides for a clearer and less confusing presentation of information to the user. Furthermore, this provides for the option to manually vary the imaging window. In doing so, the user may interactively select imaging parameters which allows adapting the presentation to the user's personal preferences and the case under consideration.

According to an embodiment, the step of generating a deformation field comprises using one or more non-rigid image registrations.

The usage of non-rigid image registrations has the advantage that non-rigid image registrations have a significantly greater flexibility in comparison to other image registrations. Non-rigid image registrations can manage local distortion between two image sets (e.g. anatomical structure changes), e.g., by applying mathematical modeling using known information to find a statistic of motion or deformation in considered organs. Further, non-rigid image registrations readily allow to take additional information into account to register sets of images, such as anatomical landmarks or image segmentations. Accordingly, non-rigid image registrations allow to reproduce non-affine organ deformations which occur in connection with patient weight loss or tissue shrinkage or swelling.

According to an embodiment, the step of generating the one or more deformation fields additionally involves using one or more (mathematical) models for soft tissue deformation.

The models may be embodied by biomechanical models which generally describe anatomical deformations in soft tissue. By construction, they do not cover pathological changes. The models may be based on macroscopic physical equations of motion as exemplified by the Navier-Cauchy equation. The model parameters may, for instance, be derived by analyzing a cohort of reference image data and follow-up image data and fitting the model to (annotated) observations. "Using" the one or more models when generating the deformation fields may mean that the deformation fields are compared to the predictions of the models or that the deformation fields are fitted to the models. In other words, "using" may mean correcting and/or smoothing the deformation fields using the one or more models. According to some embodiments, the model fitting may likewise be performed in conjunction with the image registration (i.e., as an integral step of the image registration). Since the model fitting results are "comprised" in the deformation fields and the co-aligned image data, the model fitting results are automatically provided to the machine learned network alongside the image registration results.

By using one or more models for soft tissue deformation upon generating the deformation fields, a first step of artifact correction can be performed. For instance, the comparison with the model can be used to smooth singularities and fill gaps where no information from the image registrations is present. With that, "cleaned-up" deformation fields and, thus, "cleaned-up" co-aligned image data are provided, which facilitates the further processing.

According to an embodiment, the follow-up and reference image data are magnetic resonance image data (i.e., are acquired with a magnetic resonance imaging system), wherein the reference image data is acquired using a first magnetic resonance pulse sequence, and the follow-up image data is acquired using a second magnetic resonance pulse sequence functionally different from the first sequence, preferably a double inversion recovery sequence or one or more post-contrast sequences.

"Functionally different" in this context means that for first and second magnetic resonance pulse sequences different terms and conditions apply. This may amount to different physical parameters adjusted at the MR imaging modality as well as to the controlled adjustment of different physiological conditions of the patient. The usage of two functionally different MR pulse sequences in combination with tracking pathological changes makes it possible to gather additional information by observing how one and the same region behaves for different sequences. In particular, additional information may be gleamed by analyzing the way in which a region absorbs and washes out a magnetic contrast agent. To this end, the second magnetic resonance pulse sequence may be a post-contrast sequence after a contrast agent has been administered to the patient while the first MR pulse sequence relates to a pre-contrast sequence before the contrast agent has been administered to the patient.

Alternatively, first and second pulse sequences may relate to different post-contrast sequences, i.e., sequences acquired at different points in time after a contrast agent has been administered to the patient. The sequence of post-contrast MR images may include a T1 relaxation sequence that is well suited for monitoring the absorption and washout of magnetic contrast agents. As yet a further example, the second pulse sequence may be a so-called double inversion recovery sequence using two non-selective 180°-inverting pulses. As such, double inversion recovery is a technique for suppressing signal from specific tissue or fluid types and can be used to make certain lesions more apparent and/or to not only show new but also active lesions.

According to an embodiment, the machine-learned network is trained using a loss function derived from one or more deformation fields generated by a biomechanical model of soft tissue deformation.

The biomechanical models used upon training the machine learned network may be embodied by similar models as described above in connection with the calculation of the deformation fields. As mentioned, the loss function is used to provide feedback to the network during training so that weights of the network may be adjusted to generate a better indication of the pathologically relevant changes. The loss function can be conceived as the result of a comparison of the machine learned net's output to a verified result. It is an idea of this embodiment to generate this verified result (and with that the loss function) "artificially" by calculating known anatomical deformations and artifacts from medical image data using a biomechanical motion model. In doing so, an "artificial" pair of reference image data and follow-up image data is generated of which the artifacts are known, and which can be input to the machine learned network to see if all artifacts are correctly filtered out. This has the benefit that the data available for training is augmented so that less expert-annotated reference image data and follow-up image data pairs are required for acceptable results. The training effect may be further enhanced by configuring the model such that it can simulate "artificial" pathological changes when applied to medical image data.

That being said, according to a further embodiment, a method for training a machine learned network to recognize pathological relevant changes in co-aligned image data is provided comprising a plurality of steps. A first step is directed to provide training reference image data showing a body part of a patient. A second step is directed to generate simulated follow-up image data by deforming the training reference image data using one or more models for biomechanical soft tissue deformation and, optionally, including one or more simulated pathological changes (and, further optionally, simulated artifacts in the deformation). That followed, one or more deformation fields for the training reference image data and the simulated follow-up image data describing anatomical deformations in the body part between the training reference image data and the simulated follow-up image data are calculated using one or more image registrations. A further step is directed to aligning the training reference image data and the simulated follow-up image data using the one or more deformation fields to generate co-aligned image data, followed by analyzing the co-aligned image data to identify pathological changes in the body part from the training reference image data to the simulated follow-up image data using a machine learned network. A further step is directed to compare the result with the known input generated by the one or more models for biomechanical soft tissue deformation and adjusting weights in the neural network as a function of the comparison.

Of note, the incorporation of simulated pathological changes and/or artifacts in the deformation is optional. If none of these effects is included, the machine learned network is supposed to neither identify pathological changes nor to recognize any artifacts.

Specifically, according to an embodiment, the step of comparing may comprise comparing the identified pathological changes with the simulated pathological changes.

More specifically, according to an embodiment, in the method for training a machine learned network to recognize pathological relevant changes in co-aligned image data, the step of aligning may comprise calculating deformed reference image data by applying the one or more deformation fields to the reference image data. Further, the step of analyzing comprises generating an image filter corresponding to the co-aligned image data, the image filter being configured to highlight pathological changes based on the output of the machine learned network, and subtracting the deformed reference image from the follow-up image and multiplying the result with the image filter to generate change visualization image data. Still further, the step of comparing comprises calculating a comparative image filter highlighting the simulated pathological changes and comparing the image filter with the comparative image filter.

According to an embodiment, a system for identifying pathological changes in follow-up medical images is provided. The system comprises an interface unit for receiving reference image data showing a body part of a patient at a first time and follow-up image data showing a body part of a patient at a subsequent second time. Further the system comprises a computing unit configured to: receive reference image data and follow-up image data, generate one or more deformation fields for the reference image data and the follow-up image data describing anatomical deformations in the body part between the reference image data and the follow-up image data using at least one image registration, align the reference image data and the follow up image data using the one or more deformation fields to generate co-aligned image data, and analyze the co-aligned image data to identify pathological changes in the body part from the reference image data to the follow image data using a machine learned network trained to recognize pathological relevant changes in co-aligned image data.

According to an embodiment, the system is adapted to implement an embodiment of the inventive method for identifying pathological changes in follow-up medical images. The computing unit may comprise an image registration unit configured to generate the one or more deformation fields using at least one image registration. Optionally, the registration unit may further be configured to generate the one or more deformation fields additionally based on one or more biomechanical models of soft tissue deformation. The computing unit may further comprise an aligning unit configured to generate the co-aligned image data. The computing unit is further configured to run a machined learned network for analyzing the co-aligned image data for distinguishing pathological relevant changes from anatomical deformations and artifacts stemming from the generation of the one or more deformation fields. The computing unit may further comprise a visualization unit configured to generate a visualization (for a user) highlighting the identified pathological changes against anatomical deformations and any artifacts included in the co-aligned image data, e.g., in the form of the aforementioned change visualization image data.

The computing unit may be realized as a data processing system or as a part of a data processing system. Such a data processing system can, for example, comprise a cloud-computing system, a computer network, a computer, a tablet computer, a smartphone and/or the like. The computing unit can comprise hardware and/or software. The hardware can comprise, for example, one or more processor, one or more memories and combinations thereof. The one or more memories may store instructions for carrying out the method steps according to the invention. The hardware can be configurable by the software and/or be operable by the software. Generally, all units, sub-units or modules may at least temporarily be in data exchange with each other, e.g., via a network connection or respective interfaces. Consequently, individual units may be located apart from each other.

The interface unit may comprise an interface for data exchange with a local server or a central web server via internet connection for receiving the reference image data or follow-up image data. The interface unit may be further adapted to interface with one or more users of the system, e.g., by displaying the result of the processing by the computing unit to the user (e.g., in a graphical user interface) or by allowing the user to adjust parameters for image processing or visualization and/or to select the reference image data and follow-up image data.

According to another embodiment, the invention further relates to a training system for training a machine learned network, comprising an interface, embodied for receiving the machine learned network, and further embodied for receiving training reference image data showing a body part of a patient. The training system further comprises a processor configured to generate simulated follow-up image data by deforming the training reference image data using one or more models for biomechanical soft tissue deformation and, optionally, including one or more simulated pathological changes (and, further optionally, artifacts in the deformation). The processor is further configured to calculate one or more deformation fields for the training reference image data and the simulated follow-up image data describing anatomical deformations in the body part between the training reference image data and the simulated follow-up image data. The processor is further configured to align the training reference image data and the simulated follow-up image data using the one or more deformation fields to generate co-aligned image data, and to analyze the co-aligned image data to identify pathological changes in the body part from the training reference image data to the simulated follow-up image data using a machine learned network. The processor is further configured to compare the result with the known input generated by the one or more models for biomechanical soft tissue deformation and adjusting the weights in the neural network as a function of the comparison.

In particular, such a training system can be embodied for carrying out the inventive method for training the machine learned network and its embodiments previously described. The training system is embodied to carry out this method and its embodiments, in that the interface and the processing unit are embodied to carry out the corresponding method steps.

The training system's processor may in particular involve a computer, a microcontroller or an integrated circuit. As an alternative the training system may involve a real or virtual network of computers (a real network is referred to as a cluster, a virtual network is referred to as a cloud). The interface may involve a hardware or software interface (for example PCI-Bus, USB or Firewire).

According to another embodiment, the invention further relates to an image analysis system comprising the system for identifying pathological changes in follow-up medical images and a medical image system configured to acquire, store and/or forward follow-up medical images (comprising the reference image data and the follow-up image data). Thereby, the interface unit is configured to receive the reference image data and follow-up image data from the medical image system.

According to an embodiment, the medical image system comprises one or more archive stations for storing reference image data RI and/or follow-up image data FI, which may be realized as a cloud storage or as a local or spread storage, e.g., as a PACS (Picture Archiving and Communication System). Further, the medical image system may comprise one or more medical imaging modalities, such as a computed tomography system, a magnetic resonance system, an angiography (or C-arm X-ray) system, a positron-emission tomography system, a mammography system, system for acquiring digital pathology images or the like.

According to another embodiment, the present invention is directed to a computer program product comprising program elements which induce a computing unit of a system for quantifying a medical image volume to perform the steps according to an embodiment of the method, when the program elements are loaded into a memory of the computing unit.

According to another embodiment, the present invention is directed to a computer-readable medium on which program elements are stored that are readable and executable by a computing unit of a system for quantifying a medical image volume, in order to perform steps of an embodiment of the inventive method, when the program elements are executed by the computing unit.

The realization of the invention by a computer program product and/or a computer-readable medium has the advantage that already existing providing systems can be easily adopted by software updates in order to work as proposed by at least one embodiment of the invention.

The computer program product can be, for example, a computer program or comprise another element next to the computer program as such. This other element can be hardware, e.g., a memory device, on which the computer program is stored, a hardware key for using the computer program and the like, and/or software, e.g., a documentation or a software key for using the computer program. The computer program product may further comprise development material, a runtime system and/or databases or libraries. The computer program product may be distributed among several computer instances.

In summary, embodiments of the present invention provides a method and system relying on a machine learned network for identifying pathologically relevant changes in follow up medical image data. The machine learned network is trained to filter out irrelevant changes (e.g., by training it to detect artifacts) and/or to highlight relevant (also barely visible) pathological changes based on input data which already contain a first estimate about potentially relevant pathological changes. Specifically, this input for the machine learned network is generated by combining organ-specific (non-rigid) image registrations and, optionally, motion model fitting for a whole-body part of a patient.

FIG. 1 depicts a system 1 for identifying pathological changes in follow up medical image data according to an embodiment of the present invention. System 1 is adapted to perform the method according to one or more embodiments, e.g., as further described with reference to FIG. 2 or 4.

System 1 comprises a user interface 10 (as part of the interface unit) and a processing system 20 (as part of the computing unit). Further system 1 may comprise a medical image system 40 for acquiring, storing and/or forwarding reference image data RI and follow-up image data FI. Such image studies IS for follow-up-reading may be loaded from the medical image system 40, e.g., by the processing system 20 or by the user interface 10 directly.

Reference image data RI and follow-up image data FI are three-dimensional medical image data sets acquired, for instance, using a computed tomography system or a magnetic resonance imaging system. The image information is encoded in a three-dimensional array of k times m times n voxels. Further, reference image data RI and follow-up image data FI may relate to two-dimensional medical images, for instance acquired with a X-Ray facility, with the image information being encoded in m times n pixels. Generally, reference image data RI and follow-up image data FI show the same body part of a patient at different points in time. While the reference image data RI has been taken at an earlier examination at a first time, the follow-up image data FI relates to a follow-up examination at a later stage at a second time. The second time may be hours, days, week, months, or years after the first time.

Further, there may be intervening scans or procedures between the first time and the second time. In an embodiment, the follow-up image data FI is acquired using the same or similar settings and parameters as the reference image data RI. Similar settings and parameters may include, for example, the same medical imaging modality, a same dose (if available), the same phase timing, x-ray source voltage, contrast agent, MRI-protocol, among others.

In general, the body part depicted in reference image data RI and follow-up image data FI will comprise various anatomies and organs. Considering the chest area as body part, reference image data RI and follow-up image data FI might, for instance, depict the lung lobes, the rib cage, the heart, lymph nodes, and so forth. If reference image data RI and/or follow-up image data FI relate to magnetic resonance (MR) image data of a patient (i.e., if they have been acquired using a magnetic resonance imaging system), reference image data RI and/or follow-up image data FI may have been acquired using different MR (pulse) sequences (i.e., reference image data RI has been acquired using a first MR sequence and follow-up image data FI has been acquired using a second MR sequence different than the first MR sequence).

For instance, reference image data RI and follow-up image data FI may relate to different post-contrast sequences or follow-up image data FI may relate to a post-contrast sequence while the reference image data RI has been acquired before administering the contrast agent to the patient. Further, the follow-up image data FI may be acquired using a so-called double inversion recovery sequence comprising two non-selective 180°-inverting pulses in order to suppress signals from specific tissue or fluid types. This can be used to make certain lesions more apparent and/or to not only show new but also active lesions.

User interface 10 comprises a display unit 11 and an input unit 12. User interface 10 may be embodied by a mobile device such as a smartphone or tablet computer. Further, user interface 10 may be embodied as a workstation in the form of a desktop PC or laptop. Input unit 12 may be integrated in display unit 11, e.g., in the form of a touch screen. As an alternative or in addition to that, input unit 12 may comprise a keyboard, a mouse or a digital pen and any combination thereof. Display unit 11 is configured for displaying the reference image data RI, the follow-up image data FI and/or the result of the image processing as performed by processing system 20.

User interface 10 further comprises an interface computing unit 13 configured to execute at least one software component for serving display unit 11 and input unit 12 in order to provide a graphical user interface for allowing the user to select reference image data RI and follow-up image data FI, e.g., within the graphical user interface. In addition, interface computing unit 13 may be configured to communicate with medical image system 40 or processing system 20 for receiving the reference image data RI, the follow-up image data FI and/or the result of the image processing to be displayed to the user. The user may activate the software component via user interface 10 and may acquire the software component, e.g., by downloading it from an internet application store. According to an example, the software component may also be a client-server computer program in the form of a web application running in a web browser. The interface computing unit may be a general processor, central processing unit, control processor, graphics processing unit, digital signal processor, three-dimensional rendering processor, image processor, application specific integrated circuit, field programmable gate array, digital circuit, analog circuit, combinations thereof, or other now known device for processing image data.

Processing system 20 may comprise sub-units 21-24 configured to process the reference image data RI and follow-up image data FI for identifying pathological relevant changes between the reference image data RI and follow-up image data FI. Processing system 20 may be an image processor. The image processor may be a general processor, central processing unit, control processor, graphics processing unit, digital signal processor, three-dimensional rendering processor, image processor, application specific integrated circuit, field programmable gate array, digital circuit, analog circuit, combinations thereof, or other now known device for processing image data. The image processor is a single device or multiple devices operating in serial, parallel, or separately. The image processor may be a main processor of a computer, such as a laptop or desktop computer, or may be a processor for handling some tasks in a larger system, such as in the imaging system or the server. The image processor is configured by instructions, design, hardware, and/or software to perform the steps discussed herein. Alternatively, processing system 20 may comprise a real or virtual group of computers like a so called 'cluster' or 'cloud'. Such server system may be a central server, e.g., a cloud server, or a local server, e.g., located on a hospital or radiology site. Further, processing system 20 may comprise a memory such as a RAM for temporally loading the reference image data RI and follow-up image data FI (e.g., as image study IS) from medical image system 40 for further processing. Alternatively, such memory may as well be comprised in user interface 10.

Sub-unit 21 is an image registration module or unit. It is configured to generate one or more deformation fields DF by registering reference image data RI with the follow-up image data FI and, optionally, by fitting the tracked changes with one or more motion models. For performing the image registration, sub-unit 21 may apply one or more image registration techniques comprising rigid image registrations, affine image registrations, non-rigid image registrations and any combination thereof. Further, sub-unit 21 may be configured to divide reference image data RI and follow-up image data FI into a plurality of segment pairs, e.g., according to anatomies or organs comprised in the body part. To this end, sub-unit 21 may be configured to run one or more segmentation filters, such as a lung segmentation filter, bone segmentation filter, liver segmentation filter and so forth. Sub-unit 21 may be further configured to generate individual deformation fields DF for each segment using individual image registrations and motion models (which are possibly optimized for the organ or anatomy comprised in the respective segment).

Sub-unit 22 is an aligning module or unit configured to align the reference image data RI and follow-up image data FI using the deformation fields DF as provided by sub-unit 21 in order to create co-aligned image data CAI. To this end, sub-unit 22 may be configured to transform reference image data RI and follow-up image data FI into each other's deformation state according to the calculated fields of deformation. Preferably, the transformation involves calculating deformed reference image data by applying the deformation fields DF to the reference image data RI by sub-unit 22. Alternatively, deformed follow-up image data may be calculated and further processed. As a further alternative, sub-unit 22 may merely assign the deformation fields DF to the reference image data RI and/or follow-up image data FI (without calculating any deformations) and provide this data to sub-unit 23 for further processing.

Sub-unit 23 is a module or unit configured to identify pathological changes based on the co-aligned image data CAI (the deformed reference image data). To this end, sub-unit 23 is configured to run a machine learned network 100 which has been trained to recognize pathological relevant changes in co-aligned image data CAI. Recognizing pathological changes may at least comprise recognizing any artifacts in the co-aligned image data CAI so as to distinguish artifacts from pathological relevant changes. It may further comprise actively recognizing pathological changes and, optionally, any metadata associated thereto. Specifically, the analysis result as provided by sub-unit 23 may be in the form of an image filter IF compatible with reference image data RI and follow-up image data FI. Image filter IF may be configured such that artifacts in the deformation are filtered out and/or that pathological changes are enhanced and if applied to reference image data RI and/or follow-up image data FI or any subtraction image data (see below). The machine learned model may be provided by a training module (not shown) configured to train the machine learned model.

Sub-unit 24 is a visualization module configured to translate or convert the pathological changes as identified by sub-unit 23 into a suitable representation for displaying to the user. The suitable representation can be in the form of an assistance image AI in which the pathological changes are visually encoded. This may mean that artifacts are filtered out and/or that pathological changes are enhanced in the visualization. Specifically, sub-unit 24 may be configured to subtract the deformed reference image data from the follow-up image data FI and multiplying the result with image filter IF. This will lead to image data ("change visualization image data" CVI) which contains nothing but the pathological relevant changes. Based on that, sub-unit 24 may be further configured to run or execute an algorithm for rendering a semi-transparent overlay image from the change visualization image data CVI to be superimposed over correspondingly rendered reference image data RI and/or follow-up image data FI.

Moreover, sub-unit 24 may be configured to highlight pathological changes in the form of symbols or labels in the reference image data RI and/or follow-up image data FI or to merely display the change visualization image data CVI as the assistance image AI. According to an implementation, labels may include metadata describing the type and further attributes of the identified pathological changes. Further, sub-unit 24 may be configured to "window" the visualization to user selected regions of interest in the sense that only such pathological changes are shown which lie in the region of interest. To this end, sub-unit 24 might rely on the aforementioned segmentation masks or filters to only show pathological changes within the selected anatomies or organs. Further, in particular, computed tomography image data offer a way to intensity-filter the visualization, as each voxel of CT image data usually has an intensity value that represents the attenuation of X-rays at the corresponding position in the volume as determined from the CT measurements (commonly measured in Hounsfield or HU units). Accordingly, a segmentation can be performed based solely on a thresholding of the voxel intensity values.

The designation of the distinct sub-units 21-24 is to be construed by ways of example and not as limitation. Accordingly, sub-units 21-24 may be integrated to form one single unit or can be embodied by computer code segments configured to execute the corresponding method steps running on a processor or the like of processing system 20. The same holds true with respect to interface computing unit 13. Each sub-unit 21-24 and interface computing unit 13 may be individually connected to other sub-units and or other components of the system 1 where data exchange is needed to perform the method steps. For example, sub-unit 21 may be connected to the medical image system 40 for retrieving the reference image data RI and/or follow-up image data FI and/or to interface computing unit 13 for forwarding/showing the assistance image AI to the user via user interface 10. Processing system 20 and interface computing unit 13 together may constitute the computing unit 30. Of note, the layout of computing unit 30, i.e., the physical distribution of interface computing unit 13 and sub-units 21-24 is, in principle, arbitrary. For instance, sub-unit 24 (or individual elements of it or specific algorithm sequences) may likewise be localized in user interface 10. The same holds true for the other sub-units 21-23.

Specifically, processing system 20 may also be integrated in user interface 10. As already mentioned, processing system 20 may alternatively be embodied as a server system, e.g., a cloud server, or a local server, e.g., located on a hospital or radiology site. According to such implementation, user interface 10 could be designated as "frontend" or "client" facing the user, while processing system 20 could then be conceived as "backend" or server. Communication between user interface 10 and processing system 20 may be carried out using the https-protocol, for instance. The computational power of the system may be distributed between the server and the client (i.e., user interface 10). In a "thin client" system, the majority of the computational capabilities exists at the server. In a "thick client" system, more of the computational capabilities, and possibly data, exist on the client.

Medical image system 40 is generally configured for acquiring and/or storing and/or forwarding reference image data RI and/or follow-up image data FI. For instance, medical image system 40 may comprise an archive/review station 42 for storing reference image data RI and/or follow-up image data FI. Archive/review station 42 may be realized as a cloud storage. Alternatively, archive/review station 42 may be realized as a local or spread storage, e.g., as a PACS (Picture Archiving and Communication System). Archive/review station 42 may further store further clinical information related to the reference image data RI and/or follow-up image data FI, wherein the clinical information may comprise, e.g., related medical findings, personal information related to the patient under consideration, patient records or the like. Alternatively, a further database (not shown) may store this related information. Further, medical image system 40 may comprise a medical imaging modality 41, such as a computed tomography system, a magnetic resonance system, an angiography (or C-arm X-ray) system, a positron-emission tomography system, a mammography system, system for acquiring digital pathology images or the like.

Individual components of system 1 may be at least temporarily connected to each other for data transfer and/or exchange. User interface 10 communicates with processing system 20 via interfaces to exchange, e.g., the reference image data RI and/or follow-up image data FI or the result of the computation, e.g., in the form of assistance image AI. For example, processing system 20 may be activated on a request-base, wherein the request is sent by user interface 10. Further, processing system 20 may communicate with medical image system 40 in order to retrieve one or more image studies IS comprising reference RI and follow-up image data FI. As an alternative or in addition to that, user interface 10 may communicate with medical image system 40 directly. Medical image system 40 and, in particular, archive/review station 42, may likewise be activated on a request-base, wherein the request is sent by processing system 20 and/or user interface 10. Interface for data exchange may be realized as hardware- or software-interface, e.g., a PCI-bus, USB or fire-wire. Data transfer may be realized using a network connection. The network may be realized as local area network (LAN), e.g., an intranet or a wide area network (WAN). Network connection is preferably wireless, e.g., as wireless LAN (WLAN or Wi-Fi). Further, the network may comprise a combination of different network examples. Specifically, the network may comprise a network compatible with the DICOM-standard (Digital Imaging and Communications in Medicine) and the retrieval of the reference image data RI and/or follow-up image data FI may be carried out by a DICOM query and retrieve application class. Likewise, archiving the assistance image AI in medical image system 40 may be carried out using the DICOM query and retrieve application class. Interfaces for data exchange together with the components for interfacing with the user may be regarded as constituting the aforementioned interface unit.

Figure 2A:
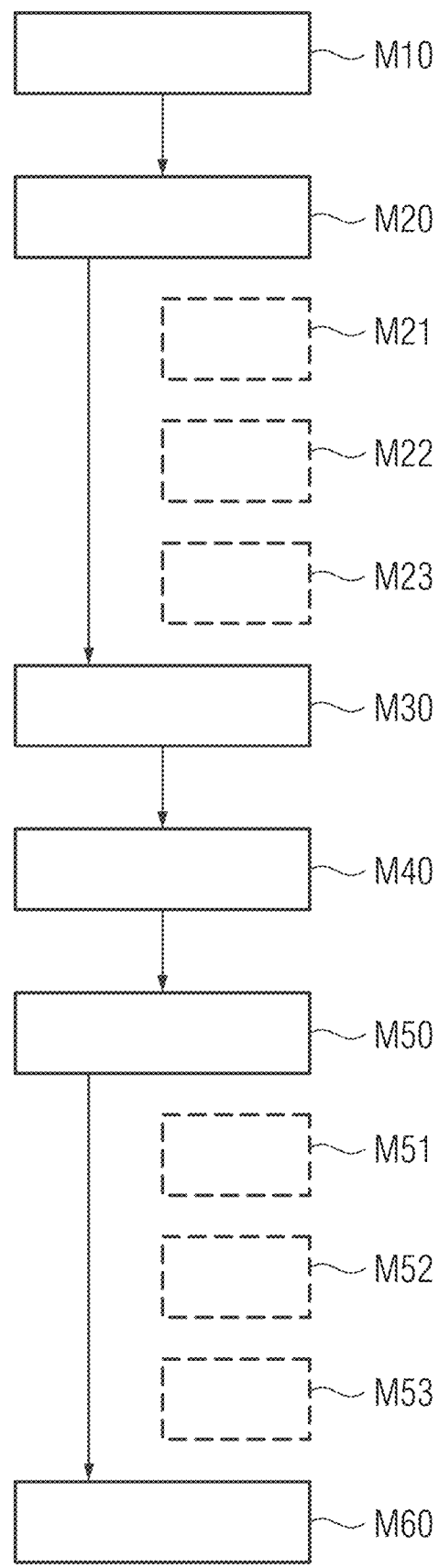
FIG. 2A depicts a flowchart illustrating a method for identifying pathological changes in follow up medical image data according to an embodiment, FIG. 2B schematically shows data streams between associated with the main method steps according to an embodiment.
Figure 2B:
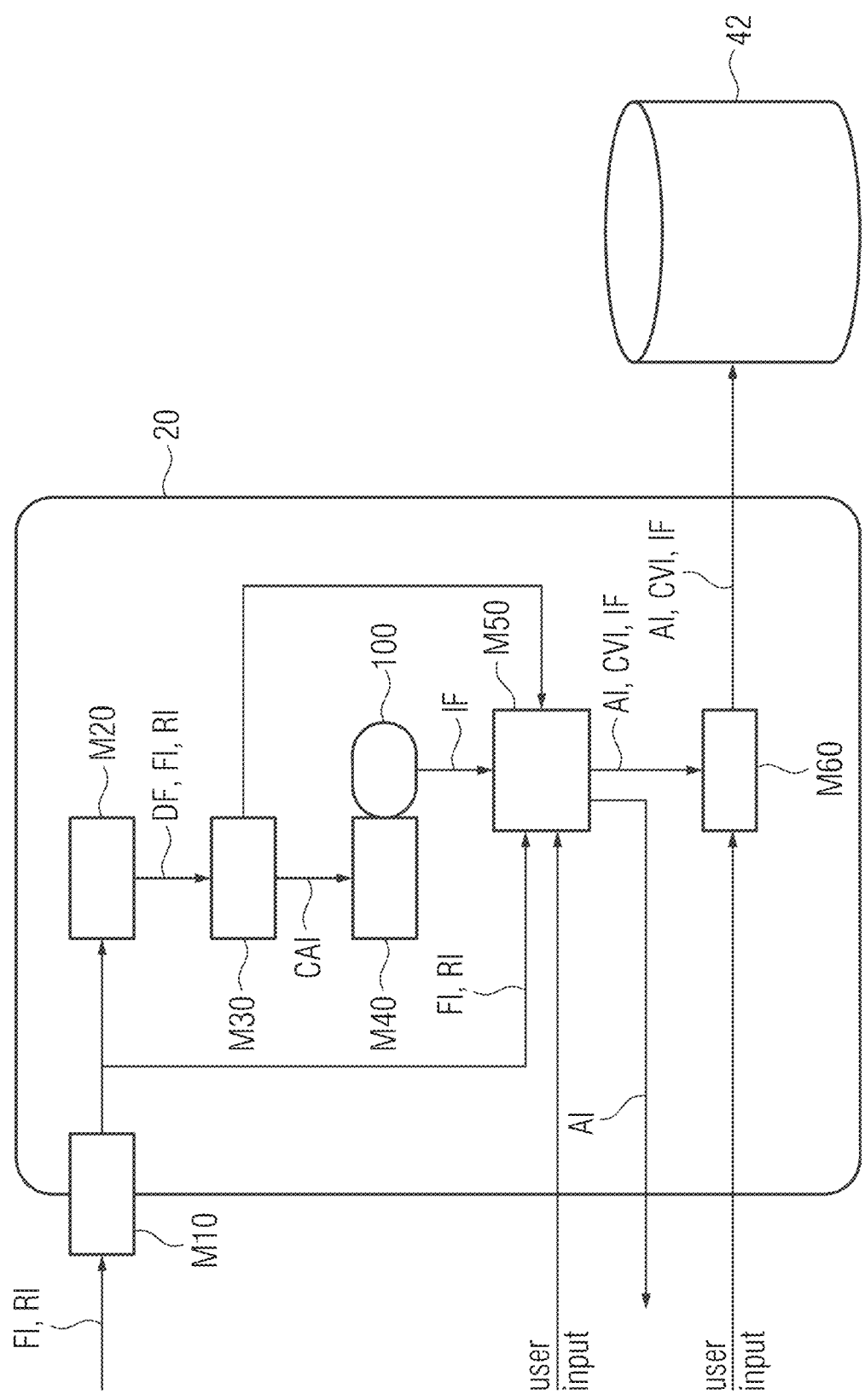

FIG. 2A depicts an inventive method for identifying pathological changes in follow-up medical images according to an embodiment of the present invention. Corresponding data streams are illustrated in FIG. 2B. The method comprises several steps. The order of the steps does not necessarily correspond to the numbering of the steps but may also vary between different embodiments of the present invention. Optional steps are shown with dashed frames in FIG. 2A.

In a first step M10, the reference image data RI and follow-up image data FI are provided (or received). This may involve selecting reference image data RI and follow-up image data FI from a plurality of follow-up images of a patient, e.g., stored in the medical image system 40. The selection may be performed manually by a user, e.g., by selecting appropriate image data in a graphical user interface running in the user interface 10. Moreover, the selection may be carried out automatically or semi-automatically by the system for users which need more assistance. In particular, this may involve automatically querying appropriate databases 42 for reference image data for a follow-up examination currently under review by the user at the user interface. Moreover, providing may involve merely receiving reference RI and follow-up image data FI. As reference image data RI and follow-up image data FI depict the same body part of the patient at different points in time, there will be variations or changes between the two image data sets. Apart from differences due to variations in alignment (which can be readily compensated by state-of-the-art auto-alignment routines), these changes mainly relate to uncritical or "healthy" deformations stemming, for instance, from the breathing motion, weight gain or loss, or the like. Such changes are also denoted as anatomical changes or deformations subsequently. Besides, there might also be pathologically relevant changes (pathological changes) that require the attention of the user. These may, for instance, relate to the occurrence of new lesions, tumor growth and shrinkage and so forth. To assist the user in deriving a medical diagnosis directed to the pathologically relevant changes, the method is up to highlight these changes for the user. To this end, it has to distinguish uncritical (anatomical) changes from relevant pathological changes. Step M10 may be performed at least partially either on user interface 10 or on processing system 20. Corresponding data exchange is included in this step where necessary.

In order to distinguish uncritical (anatomical) changes from relevant pathological changes, step M20 provides a comprehensive first estimate of the anatomical deformations in the whole-body part depicted in reference image data RI and follow-up image data FI. To this end, one or more deformation fields DF are calculated reflecting anatomic deformations between reference image data RI and follow-up image data FI. A deformation field DF can be conceived as an ensemble of deformation vectors indicative of the displacement of a voxel (or pixel) or group of voxels (pixels) from the reference image data RI to the follow-up image data FI. According to an embodiment, each voxel of the reference image data RI is assigned a deformation vector.

According to an alternative embodiment, the deformation field DF may be coarse-grained in the sense that groups of voxels (pixels) are combined and assigned a common deformation vector. In principle, the deformation fields DF are generated using image registration techniques and, in particular, non-rigid image registrations (sub-step M22). As all anatomies and organs comprised in the body part shall be appropriately addressed, it is preferred to rely on designated non-rigid image registration for individual organs and anatomies if available. If no designated non-rigid image registrations are available for certain structures of the body part, general non-rigid image registrations may be used.

In cases where splitting the image data into a plurality of image segments is not feasible, step M20 might as well comprise applying one uniform image registration only. In order to specifically apply designated non-rigid image registrations, the image registration in step M22 may be preceded by an optional sub-step M21 of segmenting reference image data RI and follow-up image data FI according to the anatomies and organs comprised in the depicted body part. Segmentation may comprise applying (in principle known) image segmentation procedures to identify and delineate organs and anatomies in reference image data RI and follow-up image data FI. For instance, a lung segmentation may be applied to identify lung lobes in reference image data RI and follow-up image data FI which facilitates the usage of image registrations specifically optimized for calculating anatomic deformations in lung tissue. Other anatomies shown in reference image data RI and follow-up image data FI may be treated similarly.

In general, using a plurality of separate image registrations will result in a plurality of deformation fields DF, which together provide an estimate of the overall anatomic deformations in the body part. Inevitably, this estimate will comprise artifacts and errors due to finite size and boundary effects where different deformation fields DF are pieced together, however. Further, not all anatomies comprised in a body part are handled equally well by image registrations.

In particular, this might apply for unstructured surrounding tissue or small and comparatively dynamic organs like lymph nodes, main vessels, intestine, pancreas and so forth. To allow for an error correction already at this stage (i.e., before actually providing the image registration result to the machine learned network 100), the result of the image registration may be fitted to one or more motion models of soft tissue deformation in optional sub-step M23. In this regard, each of the obtained deformation fields DF may be fitted separately. As an alternative or in addition to that, the overall displacement field as pieced together from the plurality of individual displacement fields may be fitted. The motion models may, for instance, be based on Navier-Cauchy equations for three-dimensional soft tissue deformation, the parameters of which are well known for certain types of tissue (e.g., from fitting the model to comparative image data or from separate experiments determining the visco-elastic properties of the underlying tissue).

In any case, the model fitting of sub-step M23 may bring about the benefit that certain artifacts in the displacement fields such as singularities, unphysical distortions or disruptions between the individual deformation fields DF are filtered out already at this stage. Further, the motion models might be used for interpolating "blank spots" of the image volume for which no deformation fields DF could be generated with image registration. Preferably, step M20 is performed in processing system 20.

In a next step M30, the deformation fields DF are used to align the reference image data RI and the follow-up image data FI. Aligning may mean that one image data set is transformed into the (deformed) coordinate system of the respective other image data set, or that, in other words, the metric of one image data set is applied to the respective other data set. Further, aligning may also amount to the (mere) assignment of a deformation vector to the underlying voxel. In any case, the co-aligned image data provides the machine learned network 100 with input data in which (visual) image information is assigned to information about the deformation state. In other words, the machine learned network 100 is thus provided with the results of the image registrations and optional model fittings in conjunction with the underlying image information. This brings the machine learned network 100 into the position to compare the deformation fields DF with the underlying image information and decide about the nature and relevance of the changes between reference image data RI and follow-up image data FI.

According to an illustrative example, the co-aligned image data is a deformed version of the reference image data RI. This deformed reference image data may be generated by applying the calculated deformation fields DF to the reference image data RI. As an alternative, the co-aligned image data may be a deformed version of the follow-up image data FI generated by applying an inverse deformation field DF to the follow-up image data FI. The deformed reference image data may be conceived as comparative data to the follow-up image data FI which comparative data has been corrected for the anatomic deformations between reference image data RI and follow-up image data FI as estimated in step M20. If the image registration in step M20 was 100% accurate, subtracting the deformed reference image data from the follow-up image data FI would result in an image data set which only comprises pathological changes which occurred in the period of time between the reference image data RI and the follow-up image data FI were taken. As image registration for whole body parts comprising a plurality of anatomies and structures is usually far from being 100% accurate, however, the subtraction image at this point will additionally comprise artifacts from improper image registrations. These are notoriously difficult to distinguish from pathological changes or, even worse, may mask pathological changes altogether. Preferably, step M30 is performed in processing system 20.

This is why, the co-aligned image data CAI is fed into the machine learned network 100 trained to identify the pathological changes for a user in ensuing step M40. Of note, "identifying" does not necessarily mean that the machine learned network 100 positively identifies the pathological changes. In order to identify the pathological changes for a user, it is in principle enough to recognize the aforementioned artifacts in the co-aligned image data CAI and filter these out as the result would already highlight the pathological changes for the user against other anatomical changes and any artifacts. The versatility of the machine learned network 100 can be enhanced, however, if the machine learned network 100 has further been trained to also recognize pathological changes in the sense of positively identifying these in the co-aligned image data CAI.

Not only this would bring about a more reliable detection of pathological changes but would also offer even more possibilities to highlight pathological changes for the user. The output of the machine learned network 100 might be provided in the form of numerical values designating coordinates and, optionally, further parameters or metadata of the pathological changes (such as, for instance, growth rate, tissue penetration, pathology type, volume, cross-section, circumference, diameter, state of the contour, degree of calcification or fat deposition, degree of solidity, and so forth).

As an alternative, the machine learned network 100 might be configured to output an image filter IF configured to filter out anatomical changes and artifacts in the deformation field DF and/or to visually enhance pathological changes in the co-aligned image data CAI. Specifically, the image filter IF may be configured such that the anatomical changes and artifacts in the deformation field DF are filtered out and/or pathological changes are enhanced if applied to the aforementioned subtraction image data (generated by subtracting the deformed reference image data from the follow-up image data FI). As such, the image filter IF may be considered as a weighted mask for bringing pathological changes to the attention of the user. Moreover, the image filter will have the same or at least a similar format as the reference image data RI and follow-up image data FI. If reference image data RI and follow-up image data FI relate to three-dimensional volumes, the image filter IF will as well, with voxel entries suited to provide for the intended filtering and/or enhancement at places where artifacts and/or pathological changes have been recognized. "Enhanced", in particular, may relate to a visual enhancement for the user, as can be provided for by assigning a specific color scheme or heat map to the pathological changes, e.g., according to the identified growth rates or malignancy.

Further, symbols may be assigned to the pathological changes making them easily traceable for the user. In addition, the color saturation, brightness or luminescence of pathological changes may be enhanced against the background. Preferably, step M40 is performed in processing system 20.

In subsequent step M50, the results as provided by the machine learned network 100 are used to generate a visualization for the user. In general, the visualization may comprise rendering one or more representation of the follow-up image data FI with the pathological changes highlighted for the user, e.g., as mentioned, by introducing symbols, applying color maps or heatmaps, and/or adjusting brightness or luminescence values. The result of the rendering can be in the form of one or more assistance images AI indicating to the user where the pathological changes are and/or what magnitude they have. The rendering may be a two-dimensional rendering on the basis of an appropriate representation of the follow-up image data FI such as a cross-section or slice through the image volume. The representation may be selected manually by the user, e.g., by scrolling through the follow-up image data FI, or (semi-) automatically by the system. Further, known volumetric rendering techniques such as ray-tracing, ray-casting or the like may be employed.

In this regard, the user may specify parameters such as the viewing angle or the viewing distance. Preferably, this can be done in an interactive manner via user interface 10 with the help of a suited graphical user interface. One specific way to highlight the pathological changes is, as mentioned, to subtract the co-aligned images from one another, e.g., by subtracting the deformed reference image data from the follow-up image data FI (sub-step M51). The result can then be multiplied with the image filter IF in sub-step M52 thereby filtering out residual artifacts in the subtraction image and/or highlighting pathological changes.

The resulting corrected difference image (which is also referred to as "change visualization image data"—CVI) can be conceived as image data as well—which, by construction, should only contain entries for such voxels belonging to pathological changes. The change visualization data CVI may be used to generate overlays over the follow-up image data FI or as additional information upon volumetric rendering of the follow-up image data FI. The change visualization data CVI will have the largest magnitudes in areas of large change, such as the border around an expanding tumor or indications of tissue diseases like emphysema. The magnitude of the change may be visualized as a heatmap, e.g., as an overlay image on the follow-up image data FI to help guide the image reading by the user. Here, a color gradient having a given color spectrum may be assigned to the magnitude of changes so that large positive changes (growth, newly occurring lesions etc.) are associated with one end of the color spectrum and large negative changes (shrinkage, disappearance) are associated to the other end of the color spectrum.

Further, the visualization may optionally be constricted or "windowed" to only provide information for regions or image segments that are of interest to the user. With that, it can be prevented that the assistance image AI is obscured with information outside of the region of interest. On the one hand, such "imaging window" may be implemented using segmentation masks or filters to only show pathological changes within anatomies or organs as selected by the user. Further, when processing CT image data, the HU intensity filter currently applied by the user may be read and the visualization may then be adapted on that basis. If, for instance, a HU window is selected by the user, the method may automatically determine which regions of the image data are still within the applied imaging window and only show such pathological changes that lie within these regions.

The results provided to the user may be enhanced with metadata further describing the identified pathological changes. The metadata may be used to create labels which may be directly included in the above-mentioned rendering of the follow up image data at corresponding positions where pathological changes have been identified. As an alternative or in addition to that, the metadata may be used to generate a list or table of the pathological changes for the user, comprising the identified pathological changes in conjunction with the corresponding metadata. Step M50 may be performed at least partially either on user interface 10 or on processing system 20. Corresponding data exchange is included in this step where necessary. Preferably, step M50 is performed in processing system 20.

In optional step M60, the result of the processing of steps M10-M50 is forwarded to the medical image system 40 for archiving the results for later use alongside with the reference image data RI and follow-up image data FI. In terms of results, any output of the machine learned network 100 and any outcome of the ensuing further processing steps may be archived, in particular, image filter IF, change visualization image data CVI and/or the assistance images AI. Moreover, the list may be exported in the form of a structured report. Preferably, step M60 is implemented such that the user has to actively decide whether or not she or he wants the evaluation results to be archived. This can be realized by a corresponding button in the graphical user interface running in user interface 10, for instance. Step M60 may be performed at least partially either on user interface 10 or on processing system 20. Corresponding data exchange is included in this step where necessary.

Figure 3:
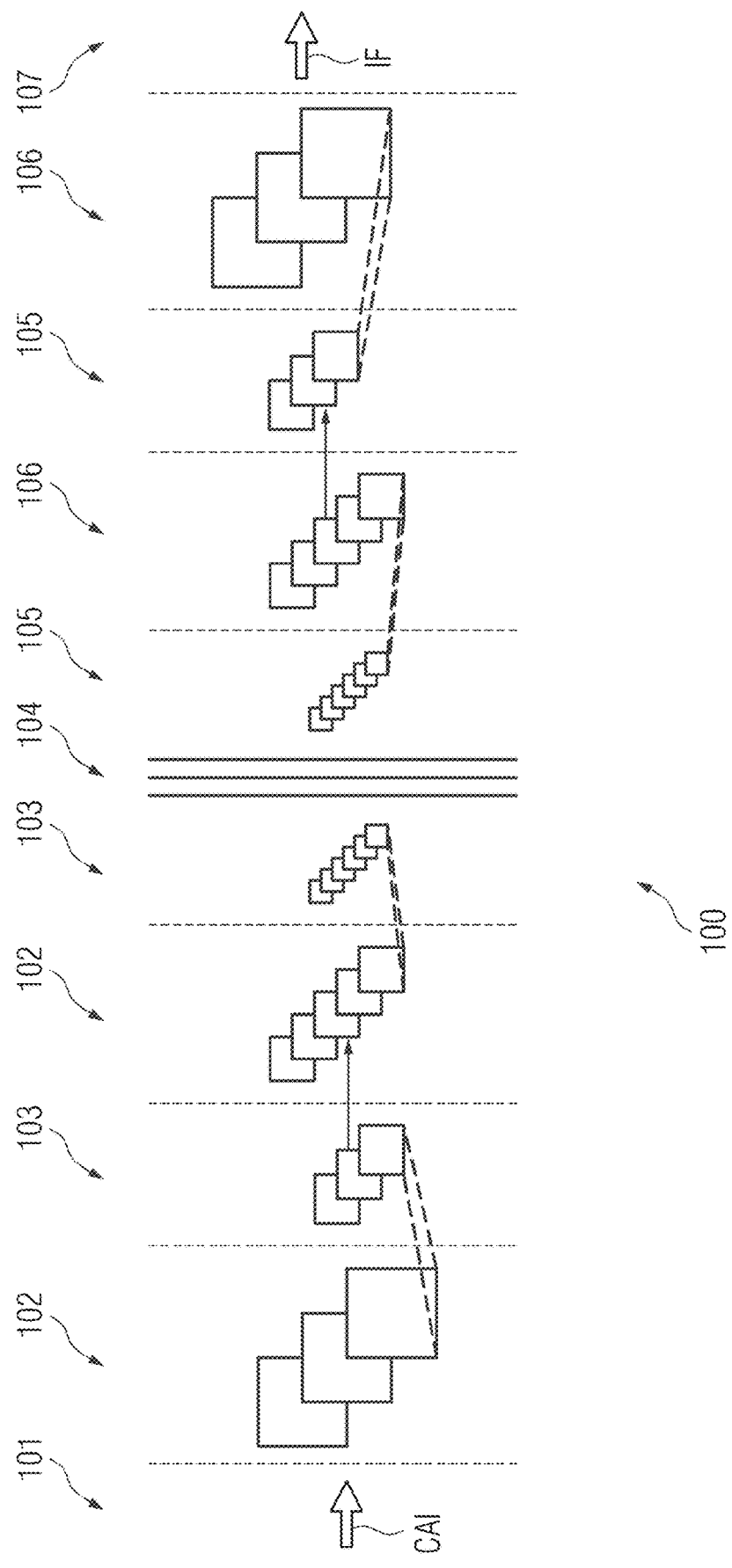
FIG. 3 depicts a machine learned network according to an embodiment.

FIG. 3 depicts an example representation of an image-to-image machine learned network 100 trained to identify pathological changes, e.g., by outputting an image filter IF or by providing coordinates of pathological relevant changes. Image filter IF may be configured to suppress artifacts in the deformation field DF and/or enhancing pathological changes (e.g., if multiplied with the reference image data RI or follow-up image data FI). In any case, the network's 100 output is indicative of pathologically relevant changes between the reference image data RI and follow-up image data FI against anatomical deformations and artifacts comprised in the co-aligned image date CAI. The machine-learned network 100 takes as input the co-aligned image data CAI and is thereby provided with the image registration results (optionally including any model fitting results) alongside with the underlying (visual) image information in the form of reference image data RI and/or follow-up image data FI. In one embodiment, the arrangement of the machine-learned network 100 is a neural network for deep learning. Other network arrangements may be used, such as a support vector machine. Deep architectures include convolutional neural networks (CNN) or deep belief nets (DBN). In an embodiment, the arrangement of the machine learned network 100 is a fully convolutional network (FCN). Alternative network arrangements may be used, for example, a 3D Very Deep Convolutional Networks (3D-VGGNet). A VGGNet stacks many layer blocks containing narrow convolutional layers followed by max pooling layers.

The machine-learned network 100 is defined in the form of a plurality of sequential layers 101-107. The term sequential is used to indicate the general flow of output feature values from one layer to input to a next layer. The information from the next layer is fed to a next layer, and so on until the final output layer. Layers 101-107 may only feed forward or may be bi-directional, including some feedback to a previous layer. The layers 101-107 may be weighted. Further, each layer 101-107 generally comprises a number of nodes that are also weighted. Essentially, each node can be seen as executing a mathematical operation mapping one or more input values to an output value. The nodes of each layer may connect with all or only a sub-set of nodes of a previous and/or subsequent layer. Two nodes are "connected" if their inputs and/or outputs are connected. Further, skip connections may be used, so that layers may also output to other layers than the sequentially next layer.

In the example shown in FIG. 3, layer 101 is the input layer. Input values for the nodes of layer 101 are image element values, preferably voxel values, and the deformation fields DF of the co-aligned image data CAI. Layer 107 is the output layer. Output values of the nodes of output layer 107 may be image element values of the image filter FI. As an alternative, output layer 107 may indicate pathological changes by outputting corresponding coordinates and values for the associated amount of change. In between input 101 and output layer 107 there is a number of hidden layers 102-106. Various layers may be used, such as convolutional 102, pooling 103 (e.g., max-pooling or average-pooling), up-sampling 105, deconvolutional 106, fully connected 104, or other types of layers. Convolutional layers convolve the input and pass its result to the next layer by moving an image filter kernel over the input. Pooling layers 103 reduce the dimensions of the data by combining the outputs of node clusters at one layer into a single node in the next layer, thereby streamlining the underlying computation. Up-sampling 105 and deconvolution layers 106 reverse the actions of convolution 102 and pooling layer 103 in terms of the abstraction level to reconstruct the output image (i.e., the image filter IF). A fully connected layer 104 connects every node in one layer to every node in another layer, so that essentially every feature gets a "vote".

The machine-learned network 100 of this embodiment learns by adapting weights or weighting parameters of individual layers and nodes based on training data. Rather than pre-programming potential artifacts or pathological changes and trying to identify these in the co-aligned image data CAI, the machine learned network architecture is defined to learn these patterns at different levels of abstraction based on input data. The learning may be conceived as learning lower-level features (i.e., features at a more abstract or compressed level) of the pathological changes and/or deformation artifacts which are common and from which pathological changes and/or deformation artifacts may be reconstructed. What is more, in the machine learned network 100, this process is cascaded since in each layer learns features for reconstructing the features of the previous layer are learned, providing more abstraction (c.f., layers 102-104). In general, for convolution, subsequent units have more abstraction.

Each node of a layer may be considered representing a feature. Different layers are provided for learning different features. To give an illustrative example, one feature may be a line directly found in the co-aligned image data CAI. The next layer may combine lines, so that one of the new features is a corner or intersection. The next layer may combine features (e.g., the corner and length of lines) from a previous layer so that the next layer provides a shape indication. For transposed convolution to reconstruct the result, the level of abstraction reverses (c.f. layers 105-106). Each layer then reduces the level of abstraction or compression.

The machine learned network 100 may preferably be trained using a method according to supervised learning. Well established is the backpropagation method, which may be applied for embodiments of the present invention. During training, the machine learned network 100 is applied to training input values to produce corresponding output values the target values of which are known. The difference between produced and target output values (e.g., in the form of the mean squared error (MSE) of the difference between produced and target values) may be used to introduce a cost or loss function as a measure of how good or bad the machine learned network 100 performs. The goal of the training is to find a (local) minimum of the loss function by iteratively adjusting the weights of the machine learned network 100 so that the machine learned network 100 is finally enabled to generate acceptable results across a (sufficiently) large cohort of training data. This optimization problem can be carried out using stochastic gradient descent or other approaches known in the art.

FIG. 4 depicts an inventive method for training a machine learned network 100 to recognize pathological changes if provided with (a) deformation field(s) DF between reference image data RI and follow-up image data FI, the deformation fields being generated by one or more image registrations and (b) the image data from reference image data RI and/or follow-up image data FI. The method comprises several steps. The order of the steps does not necessarily correspond to the numbering of the steps but may also vary between different embodiments of the present invention. Optional steps are shown with dashed frames in FIG. 4.

A first step T1 is directed to provide a plurality of training reference image data sets TRI. The training reference image data sets TRI are preferably of the same type as the image data to be processed by the deployed and readily trained machine learned model. Accordingly, the training reference image data sets TRI each likewise show a body part of a patient comprising a plurality of anatomic structures and organs and have been acquired using one of the abovementioned medical imaging modalities.

A subsequent step T10 is directed to generate a plurality of simulated follow up image data sets SFI by deforming each training reference image data set TRI using one or more biomechanical models of soft tissue deformation (subsequently also called "motion models"). The models can be of the same kind as described before in connection with step M20. Alternatively, specifically adapted models might be used. According to an embodiment, the motion models may be applied in an "organ specific" fashion so that every organ and/or anatomy comprised in the training reference image data is deformed by applying a designated motion model. In this case, the step of deforming T10 might be preceded by a step of recognizing anatomic structures in the training reference image data. Especially, if a plurality of motion models is pieced together to define the simulated follow-up image data SFI, the result is already prone to comprise a plurality of artifacts in the deformation fields DF as boundaries between organs are usually not handled well by motion models. Further, additional artifacts may be simulated upon generating the simulated follow-up image data SFI (c.f., optional sub-step T11), e.g., by a designated modelling module mimicking common artifacts in image registration. Like before, artifacts relate to non-physiological (non-anatomic) deformations which arise from image processing.

Further, pathological changes may be simulated as well (c.f., optional sub-step T12), e.g., by applying a designated modelling module to the training reference image data TRI. Here, any metadata associated to the simulated pathological changes may be simulated as well, such as type, volume, cross-section, circumference, diameter, state of the contour, degree of calcification or fat deposition, degree of solidity, and so forth.

In subsequent step T20, one or more deformation fields DF are respectively calculated between each pair of training reference image data TRI and simulated follow-up image data SFI as described before in connection with step M20. In subsequent step T30, a training co-aligned image data set is respectively generated from the pairs of training reference image data TRI and simulated follow-up image data SFI as described before in connection with step M30. In particular, the training co-aligned image data may be a deformed version of the training reference image data TRI.

Next, one training co-aligned image data is provided to the (not readily trained) machine learned model. Based on the training co-aligned image data, the machine learned model will recognize any artifacts and/or pathological changes according to the learned task in step T40 as described in connection with step M40 above. In particular, this may involve generating an image filter IF for the underlying pair of training reference image data TRI and simulated follow-up image data SFI. If the pair contained artifacts in the deformation field DF, the corresponding image filter IF is supposed to filter these out. Further, the image filter IF may be supposed to enhance pathological changes if any.

The performance of the machine learned model (i.e., the quality of the image filter) is evaluated in subsequent step T50. One way of implementing this would be comparing corresponding change visualization data CVI voxel-by-voxel (pixel-by-pixel). As explained above in connection with step M50, this involves subtracting the deformed training reference image data TRI from the simulated follow-up image data SFI and multiplying the result with the image filter IF. As the result should only contain (optionally highlighted) pathological changes (if any), it can be compared to a representation of the simulated pathological changes (in a desirable highlighting) in an otherwise empty image data set of the format of the training reference image data TRI. If no pathological changes are present this comparative data will be empty altogether—as should be the change visualization data CVI. Another way of implementing the comparison would be comparing the image filters generated by the machine learned network 100 to corresponding image filters respectively computed from the knowledge about the simulated pathological changes.

The comparison is used as a loss function to adjust weights of the machine learned network 100 (step T60). At step T70 the steps of identifying pathological changes by the machine learned network 100 (step T40) and comparing the result to the known output (step T50) are repeated with paired sets of training reference image data TRI and simulated follow-up image data SFI until the machine learned network 100 is able to generate results that are acceptable (i.e., until a local minimum of the loss function is reached). Once all pairs have been used, pairs are randomly shuffled for the next pass.

Of note, the training based on simulated follow-up image data SFI is preferably complemented by training based on "real" pairs of follow up image data in which the physiological changes have been appropriately annotated and highlighted by an expert.

Wherever meaningful, individual embodiments or their individual embodiments and features can be combined or exchanged with one another without limiting or widening the scope of the present invention. Advantages which are described with respect to one embodiment of the present invention are, wherever applicable, also advantageous to other embodiments of the present invention.

The following points are also part of the disclosure:

1. Computer-implemented method for identifying pathological changes in follow-up medical images, the method comprising:
   receiving reference image data showing a body part of a patient at a first time;
   receiving follow-up image data showing a body part of a patient at a subsequent second time;
   generating one or more deformation fields for the reference image data and the follow-up image data describing anatomical deformations in the body part between the reference image data and the follow-up image data using at least one image registration;
   aligning the reference image data and the follow up image data using the one or more deformation fields to generate co-aligned image data;
   analyzing the co-aligned image data to identify pathological changes in the body part from the reference image data to the follow image data using a machine learned network trained to recognize pathological relevant changes and/or artifacts stemming from the step of generating in co-aligned image data.

2. Method according to 1,
   wherein the step of aligning comprises calculating deformed reference image data by applying the one or more deformation fields to the reference image data;
   further with the step of subtracting the deformed reference image data from the follow-up image data to generate subtraction image data;
   wherein, in the step of analyzing, the machine learned network is trained to output an image filter configured to highlight pathological changes when multiplied with the subtraction image data;
   further with the steps of multiplying the image filter with the subtraction image data and visualizing the result to a user.

3. Method according to 2, further with the steps of
   determining an imaging window as selected by the user for displaying reference and/or follow-up image data; and
   applying the imaging window to the step of
   visualizing the result, and/or
   generating the one or more deformation fields, and/or
   analyzing the co-aligned image data.

4. Method according to 3, wherein reference image data and follow-up image data are computed tomography image data and the imaging window is a HU-window as selected by the user.

5. Method according to 2 to 4, wherein visualizing comprises
   rendering an image of the result;
   rendering a second image of the follow image data;
   overlaying the image over the second image.

6. Method according to any of the preceding points, further with the step of
   defining a plurality of image segments in reference image data and follow-up image data so that each image segment in the reference image data has a corresponding image segment in the follow-up image data;

selecting for each of the segments a separate image registration;

wherein the step of generating comprises generating, for each of the image segments, a separate deformation field by respectively the separate image registrations.

7. Method according to 6, wherein the step of generating comprises assembling the deformation field using the separate deformation field.

8. Method according to 6 or 7, further with the steps of
selecting for each of the image segments a separate motion model for soft tissue deformation; and
fitting each of the separate deformation fields to the selected separate motion model.

9. Method according to any of the preceding points wherein the machine learned network is a convolutional neural network, preferably an image-to-image convolutional neural network.

10. Method according to any of the preceding points,
wherein the step of identifying pathological changes comprises determining metadata associated to the pathological changes, and
further with the step of labeling the pathological changes for a user on the basis of the corresponding metadata.

11. System for identifying pathological changes in follow-up medical images, comprising:
a medical image system configured to archive and/or acquire medial image data;
an interface unit for receiving, form the medical image facility, reference image data showing a body part of a patient at a first time and follow-up image data showing a body part of a patient at a subsequent second time;
a computing unit configured to:
receive reference image data and follow-up image data;
generate one or more deformation fields for the reference image data and the follow-up image data describing anatomical deformations in the body part between the reference image data and the follow-up image data using at least one image registration;
align the reference image data and the follow up image data using the one or more deformation fields to generate co-aligned image data;
analyze the co-aligned image data to identify pathological changes in the body part from the reference image data to the follow image data using a machine learned network trained to recognize pathological relevant changes in co-aligned image data.

12. System according to 11, wherein the medical image system comprises:
one or more medical imaging modalities, preferably selected from the group of: computed tomography system, magnetic resonance system, angiography system, a positron-emission tomography system and any combination thereof; and/or
one or more medical image archiving systems, preferably, one or more picture archiving and communication systems (PACS).

Although the present invention has been disclosed in the form of preferred embodiments and variations thereon, it will be understood that numerous additional modifications and variations could be made thereto without departing from the scope of the invention. For the sake of clarity, it is to be understood that the use of "a" or "an" throughout this application does not exclude a plurality, and "comprising" does not exclude other steps or elements. The mention of a "unit" or a "device" does not preclude the use of more than one unit or device.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for identifying pathological changes in follow-up medical images, the computer-implemented method comprising:
providing reference image data showing a body part of a patient at a first time;
providing follow-up image data showing the body part of the patient at a second time, the second time being after the first time;
generating one or more first deformation fields for the reference image data and the follow-up image data using at least one image registration, the one or more first deformation fields describing anatomical deformations in the body part between the reference image data and the follow-up image data;
aligning the reference image data and the follow-up image data using the one or more first deformation fields to generate co-aligned image data; and
analyzing the co-aligned image data to identify pathological changes using a machine learned network, the pathological changes occurring in the body part of the patient between the first time and the second time, and the machine learned network being trained to identify pathological changes in the co-aligned image data.

2. The computer-implemented method of claim 1, wherein the aligning includes calculating deformed reference image data by applying the one or more first deformation fields to the reference image data.

3. The computer-implemented method of claim 2, further comprising:
subtracting the deformed reference image data from the follow-up image data; and
multiplying a result of the subtracting with an image filter.

4. The computer-implemented method of claim 1, wherein the analyzing includes generating an image filter based on the machine learned network, the image filter corresponding to the co-aligned image data, and the image filter being configured to highlight the pathological changes in the body part.

5. The computer-implemented method of claim 1, further comprising:
defining a plurality of corresponding image segments in the reference image data and the follow-up image data, wherein the generating of the one or more first deformation fields includes generating a separate deformation field for each image segment among the plurality of corresponding image segments by applying a separate image registration for each image segment among the plurality of corresponding image segments, each separate deformation field being among the one or more first deformation fields, and each separate image registration being among the at least one image registration.

6. The computer-implemented method of claim 1, further comprising:
rendering an image of the follow-up image data; and
displaying the image, the image highlighting the pathological changes in the body part.

7. The computer-implemented method of claim 6, further comprising:
determining an imaging window for at least one of the reference image data or the follow-up image data; and
at least one of rendering or displaying only parts of the image within the imaging window.

8. The computer-implemented method of claim 1, wherein the at least one image registration includes one or more non-rigid image registrations.

9. The computer-implemented method of claim 1, further comprising:
fitting the one or more first deformation fields to one or more motion models for soft tissue deformations.

10. The computer-implemented method of claim 1, wherein
the follow-up image data and the reference image data are magnetic resonance image data;
the reference image data is acquired using a first magnetic resonance pulse sequence; and
the follow-up image data is acquired using a second magnetic resonance pulse sequence, the second magnetic resonance pulse sequence being different from the first magnetic resonance pulse sequence.

11. The computer-implemented method of claim 10, wherein
the second magnetic resonance pulse sequence is a double inversion recovery sequence or a post-contrast sequence.

12. The computer-implemented method of claim 1, wherein the machine learned network is trained using a loss function derived from one or more second deformation fields generated by a biomechanical model of soft tissue deformation.

13. A non-transitory computer program product storing program elements which cause one or more processors of a system for identifying pathological changes in follow-up medical images, to perform the computer-implemented method of claim 1, when the program elements are executed by the one or more processors.

14. A non-transitory computer-readable medium storing program elements, readable and executable by one or more processors of a system for identifying pathological changes in follow-up medical images, to perform the computer-implemented method of claim 1, when the program elements are executed by the one or more processors.

15. A method for training a machine learned network including a neural network to identify pathological changes in follow-up medical images, the method comprising:
providing training reference image data showing a body part of a patient;
generating simulated follow-up image data by deforming the training reference image data using one or more models for biomechanical soft tissue deformation;
calculating one or more deformation fields for the training reference image data and the simulated follow-up image data using at least one image registration, the one or more deformation fields describing anatomical deformations in the body part between the training reference image data and the simulated follow-up image data;
aligning the training reference image data and the simulated follow-up image data using the one or more deformation fields to generate co-aligned image data;
analyzing the co-aligned image data to identify pathological changes using the machine learned network, the pathological changes occurring in the body part from the training reference image data to the simulated follow-up image data;
comparing a result of the analyzing with a known input based on the one or more models for biomechanical soft tissue deformation; and
adjusting weights in the neural network based on the comparing.

16. The method of claim 15, wherein the simulated follow-up image data includes one or more simulated pathological changes.

17. A non-transitory computer program product storing program elements which cause one or more processors of a system for identifying pathological changes in follow-up medical images, to perform the method of claim 15, when the program elements are executed by the one or more processors.

18. A non-transitory computer-readable medium storing program elements, readable and executable by one or more processors of a system for identifying pathological changes in follow-up medical images, to perform the method of claim 15, when the program elements are executed by the one or more processors.

19. A system for identifying pathological changes in follow-up medical images, the system comprising:
an interface unit configured to receive reference image data showing a body part of a patient at a first time, and to receive follow-up image data showing the body part of the patient at a second time, the second time being after the first time; and
at least one processor configured to execute computer-readable instructions to
generate one or more deformation fields for the reference image data and the follow-up image data using at least one image registration, the one or more deformation fields describing anatomical deformations in the body part between the reference image data and the follow-up image data,
align the reference image data and the follow-up image data using the one or more deformation fields to generate co-aligned image data, and
analyze the co-aligned image data to identify pathological changes using a machine learned network, the pathological changes occurring in the body part of the patient between the first time and the second time, and the machine learned network being trained to identify pathological changes in the co-aligned image data.

20. The system of claim 19, wherein the at least one processor is configured to execute computer-readable instructions to:
align the reference image data and the follow-up image data including calculating deformed reference image data by applying the one or more deformation fields to the reference image data; and
analyze the co-aligned image data by generating an image filter based on the machine learned network, the image filter corresponding to the co-aligned image data, and the image filter being configured to highlight the pathological changes in the body part.

21. The system of claim 20, wherein the at least one processor is configured to execute computer-readable instructions to:
subtract the deformed reference image data from the follow-up image data; and
multiply a result of the subtraction with the image filter.

* * * * *